United States Patent
Bowling et al.

(10) Patent No.: US 10,512,509 B2
(45) Date of Patent: Dec. 24, 2019

(54) SYSTEMS AND METHODS FOR ESTABLISHING VIRTUAL CONSTRAINT BOUNDARIES

(71) Applicant: Stryker Corporation, Kalamazoo, MI (US)

(72) Inventors: David Gene Bowling, Los Ranchos de Albuquerque, NM (US); Donald W. Malackowski, Schoolcraft, MI (US); José Luis Moctezuma de la Barrera, Freiburg (DE); Patrick Roessler, Merzhausen (DE); Jerry A. Culp, Kalamazoo, MI (US); John Michael Stuart, Rio Rancho, NM (US); Joel N. Beer, Albuquerque, NM (US)

(73) Assignee: Stryker Corporation, Kalamazoo, MI (US)

( * ) Notice: Subject to any disclaimer, the term of this patent is extended or adjusted under 35 U.S.C. 154(b) by 255 days.

(21) Appl. No.: 15/416,717

(22) Filed: Jan. 26, 2017

(65) Prior Publication Data
US 2017/0143432 A1    May 25, 2017

Related U.S. Application Data

(62) Division of application No. 14/205,702, filed on Mar. 12, 2014, now Pat. No. 9,603,665.

(Continued)

(51) Int. Cl.
*A61B 34/20* (2016.01)
*A61B 34/30* (2016.01)
(Continued)

(52) U.S. Cl.
CPC .............. *A61B 34/20* (2016.02); *A61B 17/02* (2013.01); *A61B 17/16* (2013.01); *A61B 34/30* (2016.02);
(Continued)

(58) Field of Classification Search
CPC ......... A61B 17/02; A61B 34/32; A61B 34/30; A61B 90/03; A61B 34/20; A61B 17/16;
(Continued)

(56) References Cited

U.S. PATENT DOCUMENTS 5,820,623 A    10/1998    Ng
5,824,085 A    10/1998    Sahay et al.
(Continued)

FOREIGN PATENT DOCUMENTS

CN    101254103 A    9/2008
EP    1545368 B1    3/2009
(Continued)

OTHER PUBLICATIONS

English language abstract for JP 2005-532890 extracted from espacenet.com database on Feb. 8, 2018, 1 page.

(Continued)

*Primary Examiner* — Stephen Holwerda
(74) *Attorney, Agent, or Firm* — Howard & Howard Attorneys PLLC

(57) ABSTRACT

Systems and methods for establishing and tracking virtual boundaries. The virtual boundaries can delineate zones in which an instrument is not permitted during a surgical procedure. The virtual boundaries can also delineate zones in which the surgical instrument is permitted during the surgical procedure. The virtual boundaries can also identify objects or structures to be treated by the instrument or to be avoided by the instrument during the surgical procedure.

22 Claims, 7 Drawing Sheets

Related U.S. Application Data

(60) Provisional application No. 61/780,148, filed on Mar. 13, 2013.

(51) Int. Cl.
  *A61B 17/02* (2006.01)
  *A61B 34/32* (2016.01)
  *A61B 90/00* (2016.01)
  *A61B 17/16* (2006.01)
  *A61B 17/00* (2006.01)

(52) U.S. Cl.
  CPC .............. *A61B 34/32* (2016.02); *A61B 90/03* (2016.02); *A61B 2017/00734* (2013.01); *A61B 2034/2048* (2016.02); *A61B 2034/2055* (2016.02); *A61B 2034/2061* (2016.02); *A61B 2034/2068* (2016.02); *A61B 2090/3937* (2016.02); *A61B 2090/3945* (2016.02); *A61B 2090/3983* (2016.02); *Y10S 901/09* (2013.01); *Y10S 901/47* (2013.01)

(58) Field of Classification Search
  CPC .. A61B 2017/00734; A61B 2090/3983; A61B 2034/2048; A61B 2034/2055; A61B 2034/2068; A61B 2090/3945; A61B 2034/2061; A61B 2090/3937; Y10S 901/09; Y10S 901/47
  See application file for complete search history.

(56) References Cited

U.S. PATENT DOCUMENTS

| | | |
|---|---|---|
| 5,871,018 A | 2/1999 | Delp et al. |
| 5,880,976 A | 3/1999 | DiGioia, III et al. |
| 5,882,206 A | 3/1999 | Gillio |
| 5,891,157 A | 4/1999 | Day et al. |
| 5,950,629 A | 9/1999 | Taylor et al. |
| 5,952,796 A | 9/1999 | Colgate et al. |
| 5,971,976 A | 10/1999 | Wang et al. |
| 5,976,156 A | 11/1999 | Taylor et al. |
| 5,995,738 A | 11/1999 | DiGioia, III et al. |
| 6,002,859 A | 12/1999 | DiGioia, III et al. |
| 6,033,415 A | 3/2000 | Mittelstadt et al. |
| 6,037,927 A | 3/2000 | Rosenberg |
| 6,063,095 A | 5/2000 | Wang et al. |
| 6,097,168 A | 8/2000 | Katoh et al. |
| 6,102,850 A | 8/2000 | Wang et al. |
| 6,157,873 A | 12/2000 | DeCamp et al. |
| 6,205,411 B1 | 3/2001 | DiGioia, III et al. |
| 6,228,089 B1 | 5/2001 | Wahrburg |
| 6,233,504 B1 | 5/2001 | Das et al. |
| 6,236,875 B1 | 5/2001 | Bucholz et al. |
| 6,236,906 B1 | 5/2001 | Muller |
| 6,304,050 B1 | 10/2001 | Skaar et al. |
| 6,311,100 B1 | 10/2001 | Sarma et al. |
| 6,314,312 B1 | 11/2001 | Wessels et al. |
| 6,322,567 B1 | 11/2001 | Mittelstadt et al. |
| 6,329,778 B1 | 12/2001 | Culp et al. |
| 6,330,837 B1 | 12/2001 | Charles et al. |
| 6,336,931 B1 | 1/2002 | Hsu et al. |
| 6,341,231 B1 | 1/2002 | Ferre et al. |
| 6,347,240 B1 | 2/2002 | Foley et al. |
| 6,351,659 B1 | 2/2002 | Vilsmeier |
| 6,351,661 B1 | 2/2002 | Cosman |
| 6,368,330 B1 | 4/2002 | Hynes et al. |
| 6,377,839 B1 | 4/2002 | Kalfas et al. |
| 6,385,475 B1 | 5/2002 | Cinquin et al. |
| 6,385,509 B2 | 5/2002 | Das et al. |
| 6,405,072 B1 * | 6/2002 | Cosman .............. A61B 6/5247 600/426 |
| 6,408,253 B2 | 6/2002 | Rosenberg et al. |
| 6,413,264 B1 | 7/2002 | Jensen et al. |
| 6,414,711 B2 | 7/2002 | Arimatsu et al. |
| 6,421,048 B1 | 7/2002 | Shih et al. |
| 6,423,077 B2 | 7/2002 | Carol et al. |
| 6,430,434 B1 | 8/2002 | Mittelstadt |
| 6,432,112 B2 | 8/2002 | Brock et al. |
| 6,434,415 B1 | 8/2002 | Foley et al. |
| 6,436,107 B1 | 8/2002 | Wang et al. |
| 6,450,978 B1 | 9/2002 | Brosseau et al. |
| 6,456,868 B2 | 9/2002 | Saito et al. |
| 6,461,372 B1 | 10/2002 | Jensen et al. |
| 6,466,815 B1 | 10/2002 | Saito et al. |
| 6,473,635 B1 | 10/2002 | Rasche |
| 6,490,467 B1 | 12/2002 | Bucholz et al. |
| 6,491,702 B2 | 12/2002 | Heilbrun et al. |
| 6,494,882 B1 | 12/2002 | Lebouitz et al. |
| 6,501,997 B1 | 12/2002 | Kakino |
| 6,514,082 B2 | 2/2003 | Kaufman et al. |
| 6,514,259 B2 | 2/2003 | Picard et al. |
| 6,520,228 B1 | 2/2003 | Kennedy et al. |
| 6,522,906 B1 | 2/2003 | Salisbury, Jr. et al. |
| 6,533,737 B1 | 3/2003 | Brosseau et al. |
| 6,535,756 B1 | 3/2003 | Simon et al. |
| 6,542,770 B2 | 4/2003 | Zylka et al. |
| 6,620,174 B2 | 9/2003 | Jensen et al. |
| 6,665,554 B1 | 12/2003 | Charles et al. |
| 6,676,669 B2 | 1/2004 | Charles et al. |
| 6,699,177 B1 | 3/2004 | Wang et al. |
| 6,704,694 B1 | 3/2004 | Basdogan et al. |
| 6,711,432 B1 | 3/2004 | Krause et al. |
| 6,723,106 B1 | 4/2004 | Charles et al. |
| 6,728,599 B2 | 4/2004 | Wang et al. |
| 6,757,582 B2 | 6/2004 | Brisson et al. |
| 6,778,867 B1 | 8/2004 | Ziegler et al. |
| 6,785,572 B2 | 8/2004 | Yanof et al. |
| 6,785,593 B2 | 8/2004 | Wang et al. |
| 6,788,999 B2 | 9/2004 | Green |
| 6,793,653 B2 | 9/2004 | Sanchez et al. |
| 6,804,547 B2 | 10/2004 | Pelzer et al. |
| 6,827,723 B2 | 12/2004 | Carson |
| 6,837,892 B2 | 1/2005 | Shoham |
| 6,871,117 B2 | 3/2005 | Wang et al. |
| 6,892,112 B2 | 5/2005 | Wang et al. |
| 6,963,792 B1 | 11/2005 | Green |
| 6,978,166 B2 | 12/2005 | Foley et al. |
| 6,999,852 B2 | 2/2006 | Green |
| 7,006,895 B2 | 2/2006 | Green |
| 7,035,716 B2 | 4/2006 | Harris et al. |
| 7,055,789 B2 | 6/2006 | Libbey et al. |
| 7,056,123 B2 | 6/2006 | Gregorio et al. |
| 7,097,640 B2 | 8/2006 | Wang et al. |
| 7,139,601 B2 | 11/2006 | Bucholz et al. |
| 7,155,316 B2 | 12/2006 | Sutherland et al. |
| 7,158,736 B2 | 1/2007 | Sato et al. |
| 7,181,315 B2 | 2/2007 | Watanabe et al. |
| 7,204,844 B2 | 4/2007 | Jensen et al. |
| 7,206,626 B2 | 4/2007 | Quaid, III |
| 7,206,627 B2 | 4/2007 | Abovitz et al. |
| 7,215,326 B2 | 5/2007 | Rosenberg |
| 7,239,940 B2 | 7/2007 | Wang et al. |
| 7,249,951 B2 | 7/2007 | Bevirt et al. |
| 7,346,417 B2 | 3/2008 | Luth et al. |
| 7,404,716 B2 | 7/2008 | Gregorio et al. |
| 7,454,268 B2 | 11/2008 | Jinno |
| 7,466,303 B2 | 12/2008 | Yi et al. |
| 7,468,594 B2 | 12/2008 | Svensson et al. |
| 7,543,588 B2 | 6/2009 | Wang et al. |
| 7,573,461 B2 | 8/2009 | Rosenberg |
| 7,625,383 B2 | 12/2009 | Charles et al. |
| 7,648,513 B2 | 1/2010 | Green et al. |
| 7,660,623 B2 | 2/2010 | Hunter et al. |
| 7,683,565 B2 | 3/2010 | Quaid et al. |
| 7,725,162 B2 | 5/2010 | Malackowski et al. |
| 7,744,608 B2 | 6/2010 | Lee et al. |
| 7,747,311 B2 | 6/2010 | Quaid, III |
| 7,772,541 B2 | 8/2010 | Froggatt et al. |
| 7,813,838 B2 | 10/2010 | Sommer |
| 7,818,044 B2 | 10/2010 | Dukesherer et al. |
| 7,824,424 B2 | 11/2010 | Jensen et al. |
| 7,831,292 B2 | 11/2010 | Quaid et al. |
| 7,835,784 B2 | 11/2010 | Mire et al. |

(56) References Cited

U.S. PATENT DOCUMENTS

| | | | |
|---|---|---|---|
| 7,892,243 B2 | 2/2011 | Stuart | |
| 7,914,522 B2 | 3/2011 | Morley et al. | |
| 7,950,306 B2 | 5/2011 | Stuart | |
| 8,010,180 B2 | 8/2011 | Quaid et al. | |
| 8,287,522 B2 | 10/2012 | Moses et al. | |
| 8,343,048 B2 | 1/2013 | Warren, Jr. | |
| 9,119,655 B2 | 9/2015 | Bowling et al. | |
| 9,381,085 B2 | 7/2016 | Axelson, Jr. et al. | |
| 9,480,534 B2 | 11/2016 | Bowling et al. | |
| 9,603,665 B2 | 3/2017 | Bowling et al. | |
| 9,615,987 B2 | 4/2017 | Worm et al. | |
| 9,707,043 B2 | 7/2017 | Bozung | |
| 2002/0035321 A1 | 3/2002 | Bucholz et al. | |
| 2002/0120188 A1* | 8/2002 | Brock | A61B 5/0086 600/407 |
| 2003/0181800 A1* | 9/2003 | Bonutti | A61B 17/0401 600/407 |
| 2003/0208296 A1 | 11/2003 | Brisson et al. | |
| 2004/0010190 A1 | 1/2004 | Shahidi | |
| 2004/0024311 A1 | 2/2004 | Quaid | |
| 2004/0034283 A1 | 2/2004 | Quaid | |
| 2004/0034302 A1 | 2/2004 | Abovitz et al. | |
| 2004/0059194 A1 | 3/2004 | Berg et al. | |
| 2004/0077939 A1 | 4/2004 | Graumann | |
| 2004/0106916 A1 | 6/2004 | Quaid et al. | |
| 2004/0138556 A1 | 7/2004 | Cosman | |
| 2005/0171553 A1 | 8/2005 | Schwarz et al. | |
| 2006/0020279 A1* | 1/2006 | Chauhan | A61B 90/36 606/167 |
| 2006/0109266 A1 | 5/2006 | Itkowitz et al. | |
| 2006/0142657 A1 | 6/2006 | Quaid et al. | |
| 2006/0155262 A1 | 7/2006 | Kishi et al. | |
| 2006/0176242 A1 | 8/2006 | Jaramaz et al. | |
| 2007/0260394 A1 | 11/2007 | Dean | |
| 2007/0265527 A1 | 11/2007 | Wohlgemuth | |
| 2007/0270685 A1 | 11/2007 | Kang et al. | |
| 2008/0058776 A1 | 3/2008 | Jo et al. | |
| 2008/0077158 A1 | 3/2008 | Haider et al. | |
| 2008/0108912 A1 | 5/2008 | Node-Langlois | |
| 2008/0161829 A1 | 7/2008 | Kang | |
| 2008/0214898 A1 | 9/2008 | Warren | |
| 2009/0003975 A1 | 1/2009 | Kuduvalli et al. | |
| 2010/0331859 A1 | 12/2010 | Omori | |
| 2011/0106102 A1 | 5/2011 | Balicki et al. | |
| 2011/0130761 A1 | 6/2011 | Plaskos et al. | |
| 2011/0152676 A1 | 6/2011 | Groszmann et al. | |
| 2011/0263971 A1 | 10/2011 | Nikou et al. | |
| 2011/0264107 A1 | 10/2011 | Nikou et al. | |
| 2012/0059378 A1 | 3/2012 | Farrell | |
| 2012/0071752 A1 | 3/2012 | Sewell et al. | |
| 2012/0071893 A1 | 3/2012 | Smith et al. | |
| 2012/0143084 A1 | 6/2012 | Shoham | |
| 2012/0330429 A1 | 12/2012 | Axelson, Jr. et al. | |
| 2013/0006267 A1 | 1/2013 | Odermatt et al. | |
| 2013/0019883 A1 | 1/2013 | Worm et al. | |
| 2013/0060278 A1 | 3/2013 | Bozung et al. | |
| 2013/0096574 A1 | 4/2013 | Kang et al. | |
| 2014/0005684 A1* | 1/2014 | Kim | A61B 17/0643 606/130 |
| 2014/0039681 A1 | 2/2014 | Bowling et al. | |
| 2014/0180290 A1 | 6/2014 | Otto et al. | |

FOREIGN PATENT DOCUMENTS

| | | |
|---|---|---|
| JP | 2005532890 A | 11/2005 |
| JP | 2006106419 A | 4/2006 |
| KR | 20100098055 A | 9/2010 |
| KR | 20110036453 A | 4/2011 |
| WO | 1996011624 A2 | 4/1996 |
| WO | 1999037220 A1 | 7/1999 |
| WO | 2000021450 A1 | 4/2000 |
| WO | 2000035366 A1 | 6/2000 |
| WO | 2000059397 A1 | 10/2000 |
| WO | 2000060571 A1 | 10/2000 |
| WO | 2002000131 A1 | 1/2002 |
| WO | 2002024051 A2 | 3/2002 |
| WO | 2002060653 A2 | 8/2002 |
| WO | 2002065931 A1 | 8/2002 |
| WO | 2002074500 A2 | 9/2002 |
| WO | 2002076302 A2 | 10/2002 |
| WO | 2003094108 A2 | 11/2003 |
| WO | 2004001569 A2 | 12/2003 |
| WO | 2004014244 A2 | 2/2004 |
| WO | 2004019785 A2 | 3/2004 |
| WO | 2004069036 A2 | 8/2004 |
| WO | 2005009215 A2 | 2/2005 |
| WO | 2006058633 A1 | 6/2006 |
| WO | 2006063156 A1 | 6/2006 |
| WO | 2006091494 A1 | 8/2006 |
| WO | 2006106419 A2 | 10/2006 |
| WO | 2007017642 A1 | 2/2007 |
| WO | 2007111749 A2 | 10/2007 |
| WO | 2007117297 A2 | 10/2007 |
| WO | 2007136739 A2 | 11/2007 |
| WO | 2007136768 A2 | 11/2007 |
| WO | 2007136769 A2 | 11/2007 |
| WO | 2007136771 A2 | 11/2007 |
| WO | 2009059330 A2 | 5/2009 |
| WO | 2011021192 A1 | 2/2011 |
| WO | 2011088541 A1 | 7/2011 |
| WO | 2011106861 A1 | 9/2011 |
| WO | 2011113483 A1 | 9/2011 |
| WO | 2011128766 A2 | 10/2011 |
| WO | 2011133873 A1 | 10/2011 |
| WO | 2011133927 A2 | 10/2011 |
| WO | 2011134083 A1 | 11/2011 |
| WO | 2012018816 A2 | 2/2012 |

OTHER PUBLICATIONS

English language abstract for JP 2006-106419 extracted from espacenet.com database on Feb. 8, 2018, 1 page.

C. Sim; S.N. Wan; Y.T. Ming; L. Yong-Chong; T.Y. Tseng, Image-Guided Manipulator Compliant Surgical Planning Methodology for Robotic Skull-Base Surgery, Medical Imaging and Augmented Reality, 2001. Proceedings. International Workshop on, Jun. 10-12, 2001, pp. 26-29, IEEE, Shatin, HK; 4 pages.

M. Fleute; S. Lavallee; R. Julliard, Incorporating a statistically based shape model into a system for computer-assisted anterior cruciate ligament surgery, Medical Image Analysis, Oct. 1999, pp. 209-222, vol. 3, No. 3, FR; 14 pages. cited byapplicant.

S.J. Harris; M. Jakopec; J. Cobb; B.L. Davies, Intra-operative Application of a Robotic Knee Surgery System, Medical Image Computing and Computer-Assisted Intervention—MICCAI'99, 1999, pp. 1116-1124, vol. 1679, Springer-Verlag Berlin Heidelberg; 9pages.

B. Haßfeld; C. Burghart; I. Bertovic; J. Raczkowsky; H. Worn; U. Rembold; J. Muhling, Intraoperative Navigation Techniques Accuracy Tests and Clinical Report, In: Computer Assisted Radiology and Surgery (CARS'98), Tokyo, Jun. 1998, pp. 670-675,Elseview Science B.V.; 6 pages.

J.E. Colgate; M.C. Stanley; J.M. Brown, Issues in the Haptic Display of Tool Use, Intelligent Robots and Systems 95. 'Human Robot Interaction and Cooperative Robots', Proceedings. 1995 IEEE/RSJ International Conference on, Aug. 5-9, 1995, pp. 140-145, vol. 3, IEEE, Pittsburgh, PA, USA; 6 pages.

G. Van Ham; K. Denis; J. Vander Sloten; R. Van Audekercke; G. Van Der Perre; J. De Schuller; E. Aertbelien; S. Demey; J. Bellemans, Machining and Accuracy Studies for a Tibial Knee Implant Using a Force-Controlled Robot, Computer Aided Surgery, Feb. 1998, pp. 123-133, vol. 3, Wiley-Liss, Inc., Heverlee BE; 11 pages.

H. Haider; O. A. Barrera and K. L. Garvin, Minimally Invasive Total Knee Arthroplasty Surgery Through Navigated Freehand Bone Cutting, Journal of Arthroplasty, Jun. 2007, vol. 22, No. 4, pp. 535-542, Elsevier B.V.; 8 pages.

C.N. Riviere and N.V. Thakor, Modeling and Canceling Tremor in Human-Machine Interfaces, Engineering in Medicine and Biology Magazine, IEEE, vol. 15, Issue 3, May/Jun. 1996, pp. 29-36, IEEE; 8 pages.

(56) References Cited

OTHER PUBLICATIONS

B.L. Davies; S. Starkie; S.J. Harris; E. Agterhuis; V. Paul; L.M. Auer, Neurobot a special-purpose robot for neurosurgery, Robotics and Automation, 2000. Proceedings. ICRA '00. IEEE International Conference on, Apr. 2000, pp. 4103-4108, vol. 4,IEEE, San Francisco, CA, USA; 6 pages.
J. Andreas B.ae butted.rentzen, Octree-based Volume Sculpting, Proc. Late Breaking Hot Topics, IEEE Visualization 98, pp. 9-12, 1998; 4 pages.
Orto Maquet and Caspar: An Automated Cell for Prosthesis Surgery, Robotics World, Sep./Oct. 1999, pp. 30-31, Circular No. 87 on Reader Reply Card; 2 pages.
G. Brisson, T. Kanade, A. Digioia and B. Jaramaz, Precision Freehand Sculpting of Bone, Medical Image Computing and Computer-Assisted Intervention—MICCAI 2004, Lecture Notes in Computer Science, vol. 3217, Jan. 1, 2004, pp. 105-112, Springer-VerlagBerlin Heidelberg 2004; 8 pages.
M. Fadda; S. Martelli; P. Dario; M. Marcacci; S. Zaffagnini; A. Visani, Premiers Pas Vers La Dissectomie et la Realisation de Protheses du Genou a L'Aide de Robots, Innov. Tech. Bio. Med. , 1992, pp. 394-409, vol. 13, No. 4; 16 pages. cited byapplicant.
W.L. Bargar; A. Bauer; M. Borner, Primary and Revision Total Hip Replacement Using the Robodoc System, Clinical Orthopaedics and Related Research, Sep. 1998, pp. 82-91, No. 354; 10 pages.
Prototype of Instrument for Minimally Invasive Surgery with 6-Axis Force Sensing CapabilityU. Seibold, B. Kubler, and G. Hirzinger, Prototype of Instrument for Minimally Invasive Surgery with 6-Axis Force Sensing Capability, Robotics and Automation,2005. ICRA 2005. Proceedings of the 2005 IEEE International Conference on, Apr. 18-22, 2005, pp. 498-503, IEEE, Barcelona, Spain; 6 pages.
B. Jaramaz; C. Nikou; D.A. Simon; A.M. Digioia III, Range of Motion After Total Hip Arthroplasty Experimental Verification of the Analytical Simulator, CVRMed-MRCAS'97, Lecture Notes in Computer Science, Feb. 20, 1997, pp. 573-582, vol. 1205,Springer Berlin Heidelberg, Pittsburgh, PA, USA; 14 pages.
J. T. Lea, D. Watkins, A. Mills, M. A. Peshkin, T. C. Kienzle, III and S. D. Stulberg, Registration and immobilization in robot-assisted surgery, Journal of Image Guided Surgery, Computer Aided Surgery, 1995, vol. 1, No. 2, pp. 80-87; 11 pages.
J. T. Lea, Registration Graphs a Language for Modeling and Analyzing Registration in Image-Guided Surgery, Dec. 1998, Evanston, Illinois, US; 49 pages.
C. Meng; T. Wang; W. Chou; S. Luan; Y. Zhang; Z. Tian, Remote surgery case robot-assisted teleneurosurgery, Robotics and Automation, 2004. Proceedings. ICRA '04. 2004 IEEE International Conference on, Apr. 26-May 1, 2004, pp. 819-823, vol. 1, IEEE,New Orleans, LA, USA; 5 pages.
B.K. Redlich; C. Burghart; R. Krempien; T. Redlich; A. Pernozzoli; H. Grabowski; J. Muenchenberg; J. Albers; S. Hafeld; C. Vahl; U. Rembold; G. Woern, Robot assisted craniofacial surgery first clinical evaluation, Computer Assisted Radiology andSurgery, 1999, pp. 828-833; 7 pages.
S.C. Ho; R.D. Hibberd; B.L. Davies, Robot Assisted Knee Surgery, IEEE Engineering in Medicine and Biology, May/Jun. 1995, pp. 292-300, vol. 14, No. 3; 9 pages.
C. Burghart; J. Keitel; S. Hassfeld; U. Rembold; H. Woern, Robot Controlled Osteotomy in Craniofacial Surgery, First International Workshop on Haptic Devices in Medical Applications Proceedings, Jun. 23, 1999, pp. 12-22, Paris, FR; 13 pages.
K. Bouazza-Marouf; I. Browbank; J.R. Hewit, Robot-assisted invasive orthopaedic surgery, Mechatronics in Surgery, Jun. 1996, pp. 381-397, vol. 6, Issue 4, UK; 17 pages.
C.R. Burghart, Robotergestutzte Osteotomie in der craniofacialen Chirurgie (Robot Clipped osteotomy in craniofacial surgery), Jul. 1, 1999, GCA-Verlag, 2000; 250 pages.
Y. Koseki; K. Chinzei; N. Koyachi; T. Arai, Robotic assist for MR-guided surgery using leverage and parallelepiped mechanism, Medical Image Computing and Computer-Assisted Intervention—MICCAI 2000, Lecture Notes in Computer Science, 2000, pp. 940-948, vol. 1935, Springer Berlin Heidelberg; 9 pages.
F. A. Matsen; J.L. Garbini; J.A. Sidles; B. Pratt; D. Baumgarten; R. Kaiura, Robotic Assistance in Orthopaedic Surgery a Proof of Principle Using Distal Femoral Arthroplasty, Clinical Orthopaedic Related Research, Nov. 1993, pp. 178-186, vol. 296; 9pages.
H. A. Paul, W. L. Bargar, B. Mittlestadt, P. Kazanzides, B. Musits, J. Zuhars, P. W. Cain, B. Williamson and F. G. Smith, Robotic Execution of a Surgical Plan, Systems, Man and Cybernetics, 1992., IEEE International Conference on, Oct. 18-21, 1992,pp. 1621-1623, IEEE, Sacramento, California, US; 3 pages.
B.L. Davies, Robotics in minimally invasive surgery, Through the Keyhole: Microengineering in Minimally Invasive Surgery, IEE Colloquium on, Jun. 6, 1995, pp. 5/1-5/2, London, UK; 2 pages.
R. Buckingham, Robotics in surgery a new generation of surgical tools incorporate computer technology and mechanical actuation to give surgeons much finer control than previously possible during some operations, IEE Review, Sep. 1994, pp. 193-196; 4pages.
R.O. Buckingham, Safe Active Robotic Devices for Surgery, Systems, Man and Cybernetics, 1993. 'Systems Engineering in the Service of Humans', Conference Proceedings., International Conference on, Oct. 17-20, 1993, pp. 355-358, vol. 5, IEEE, LeTougeut; 4 pages.
P. Shinsuk, Safety Strategies for Human-Robot Interaction in Surgical Environment, SICE-ICASE, 2006. International Joint Conference, Oct. 18-21, 2006, pp. 1769-1773, IEEE, Bexco, Busan, SK; 5 pages.
R.H. Taylor; C.B. Cutting; Y.-Y. Kim; A.D. Kalvin; D. Larose; B.Haddad; D. Khoramabadi; M. Noz; R. Olyha; N. Bruun; D. Grimm, A Model-Based Optimal Planning and Execution System with Active Sensing and Passive Manipulation for Augmentation of HumanPrecision in Computer-Integrated Surgery, Experimental Robotics II, The 2nd International Symposium, Lecture Notes in Control and Information Sciences, pp. 177-195, vol. 190, Springer Berlin Heidelberg, Toulouse, FR, Jun. 25-27, 1991; 19 pages. cited byapplicant.
C. Doignon; F. Nageotte; M. De Mathelin, Segmentation and guidance of multiple rigid objects for intra-operative endoscopic vision, Proceeding WDV'05/WDV'06/ICCV'05/ECCV'06 Proceedings of the 2005/2006 International Conference on Dynamical Vision,2006, pp. 314-327, Springer-Verlag Berlin, Heidelberg, Illkirch, FR; 14 pages.
J. Troccaz; Y. Delnondedieu, Semi-Active Guiding Systems in Surgery. A Two-DOF Prototype of the Passive Arm with Dynamic Constraints (PADyC), Mechatronics, Jun. 1996, pp. 399-421, vol. 6, Issue 4, 1996, Elsevier Ltd., UK; 23 pages. cited byapplicant.
T. J. Levison, J. E. Moody, B. Jaramaz, C. Nikou, A. M. Digioia, Surgical Navigation for THR a Report on Clinical Trial Utilizing HipNav, MICCAI 2000, LNCS 1935, pp. 1185-1187, 2000, Springer-Verlag Berlin Heidelberg; 3 pages.
U. Rembold and C. R. Burghart, Surgical Robotics: An Introduction, Journal of Intelligent and Robotic Systems vol. 30, No. 1, pp. 1-28, 2001, Kluwer Academic Publishers; 28 pages.
W. Siebert; S. Mai; R. Kober; P.F. Heeckt, Technique and first clinical results of robot-assisted total knee replacement, The Knee, Sep. 2002, pp. 173-180, vol. 9, Issue 3, Elsevier B.V.; 8 pages.
M. Jakopec; S.J. Harris; Y B.F. Rodriguez; P. Gomes; J. Cobb; B.L. Davies, The first clinical application of a "hands-on" robotic knee surgery system, Computer Aided Surgery , 2001, pp. 329-339, vol. 6, Issue 6, Wiley-Liss, Inc.; 11 pages. cited byapplicant.
E.H. Spencer, The ROBODOC Clinical Trial A Robotic Assistant for Total Hip Arthroplasty, Orthopaedic Nursing, Jan.-Feb. 1996, pp. 9-14, vol. 15, Issue 1; 6 pages.
E. Watanabe; T. Watanabe; S. Manaka; Y. Mayanagi; K. Takakura, Three-Dimensional Digitizer (Neuronavigator); New Equipment for Computed Tomography-Guided Stereotaxic Surgery, Surgical Neurology, Jun. 1987, pp. 543-547, vol. 27, Issue 6, ElsevierInc.; 5 pages.
T.C. Kienzle, III, S.D. Stulberg, M. Peshkin, A. Quaid, J. Lea, A. Goswami, C.H. Wu, Total Knee Replacement Computer-assisted surgical system uses a calibrated robot, Engineering in Medicine and Biology, May 1995, pp. 301-306, vol. 14, Issue 3,IEEE; 35 pages.

(56) References Cited

OTHER PUBLICATIONS

A. Ansara; D. Rodrigues; J.P. Desai; K. Daniilidis; V. Kumar; M. F.M. Campos, Visual and haptic collaborative tele-presence, Computers & Graphics, 2001, pp. 789-798, vol. 25, Elsevier, Inc.; 10 pages.
Machine-Assisted English language translation for WO 0021450 A1 extracted www.espacenet.com on Jul. 3, 2014; 28 pages.
Machine-Assisted English language translation for WO 0059397 A1 extracted www.espacenet.com Jul. 3, 2014; 33 pages.
Machine-Assisted English language translation for WO 02074500 extracted www.espacenet.com Apr. 30, 2014; 26 pages.
International Search Report for Application No. PCT/US2014/024269 dated Oct. 17, 2014, 6 pages.
U.S. Appl. No. 61/679,258, filed Aug. 3, 2012.
U.S. Appl. No. 61/753,219, filed Jan. 16, 2013.
English language abstract for CN 101254103 extracted from espacenet.com database on Sep. 25, 2017, 2 pages.
J L. Moctezuma, F. Gosse and H.-J. Schulz, A Computer and Robotic Aided Surgery System for Accomplishing Osteotomies, First International Symposium onMedical Robotics and Computer Assisted Surgery, Sep. 22-24, 1994, Pittsburgh, Pennsylvania, US; 6 pages.
C.B. Zilles; J.K. Salisbury, A Constraint-Based God-object Method for Haptic Display, Intelligent Robots and Systems 95. 'Human Robot Interaction and Cooperative Robots', Proceedings. 1995 IEEE/RSJ International Conference on , Aug. 5-9, 1995, pp. 146-151, vol. 3, IEEE, MIT, Cambridge, MA, USA; 6 pages.
Kato A., Yoshimine T., Hayakawa T., Tomita Y., Ikeda T., Mitomo M., Harada K. Mogami H., A frameless, armless navigational system for computer-assisted neurosurgery. Technical note, Journal of Neurosurgery, vol. 74, May 1991, pp. 845-849; 5 pages.
B. Preising; CA Davis; T.C. Hsia and B. Mittelstadt, A Literature Review Robots in Medicine, Engineering in Medicine and Biology Magazine, IEEE (vol. 10, Issue: 2), Jun. 1991, pp. 13-22, IEEE; 10 pages.
L. P. Nolte, L. Zamorano, S. Jiang, Q. Wang, F. Longlotz, E. Arm and H. Visarius, A Novel Approach to Computer Assisted Spine Surgery, Proc. First International Symposium on Medical Robotics and Computer Assisted Surgery, Pittsburgh, 1994, pp. 323-328; 7 pages.
J. Troccaz; S. Lavallee; E. Hellion, A passive arm with dynamic constraints a solution to safety problems in medical robotics, Systems, Man and Cybernetics, 1993. 'Systems Engineering in the Service of Humans', Conference Proceedings., InternationalConference on, Oct. 17-20, 1993, pp. 166-171, vol. 3, IEEE, Le Touquet, FR; 6 pages.
B. Davies, A review of robotics in surgery, Proceedings of the Institution of Mechanical Engineers, Part H: Journal of Engineering in Medicine Jan. 1, 2000, vol. 214, No. 1, pp. 129-140, Sage Publications; 13 pages.
T. Wang; M. Fadda; M. Marcacci; S. Martelli; P. Dario; A. Visani, A robotized surgeon assistant, Intelligent Robots and Systems '94. 'Advanced Robotic Systems and the Real World', IROS '94. Proceedings of the IEEE/RSJ/GI International Conference on,Sep. 12-16, 1994, pp. 862-869, vol. 2, IEEE, Munich, Germany; 8 pages.
D. Engel, J. Raczkowsky and H. Worn, A Safe Robot System for Craniofacial Surgery, Robotics and Automation, 2001. Proceedings 2001 ICRA. IEEE International Conference on (vol. 2), pp. 2020-2024, IEEE; 5 pages.
R. Taylor, P. Jensen, L. Whitcomb, A. Barnes, R. Kumar, D. Stoianovici, P, Gupta, Z. Wang, E.Dejuan and L. Kavoussi, A Steady-Hand Robotic System for Microsurgical Augementation, MICCAI99: the Second International Conference on Medical ImageComputing and Computer-Assisted Intervention, Cambridge, England, Sep. 19-22, 1999. MICCAI99 Submission #1361999, pp. 1031-1041, Springer-Verlag Berlin Heidelberg; 11 pages.
Julio J. Santos-Munne, Michael A. Peshkin , Srdjan Mirkovic , S. David Stulberg , Thomas C. Kienzle III, A Stereotactic/Robotic System for Pedicle Screw Placement, Interactive Technology and the New Paradigm for Healthcare, (Proceedings of theMedicine Meets Virtual Reality III Conference, San Diego, 1995), pp. 326-333, IOS Press and Ohmsha; 8 pages.
RE Ellis; CY Tso; JF Rudan; MM Harrison, A surgical planning and guidance system for high tibial osteotomy, Computer Aided Surgery, Apr. 16, 1999, 264-274, vol. 4, Wiley-Liss, Inc.; 11 pages.
H.A. Paul; B. Mittlestadt; W.L. Bargar; B. Musits; R.N. Taylor; P. Kazanzides; J. Zuhars; B. Williamson; W. Hanson, A Surgical Robot for Total Hip Replacement Surgery, International Conference on Robotics and Automation, 1992, pp. 606-611, IEEE,Nice, FR; 6 pages.
G. Van Ham; J. Bellemans; L. Labey; J. Vander Sloten; R. Van Audekercke; G. Van Der Perre; J. De Schutter, Accuracy study on the registration of the tibia by means of an intramedullary rod in robot-assisted total knee arthroplasty, PosterSession—Knee Arthroplasty—Valencia Foyer, 46th Annual Meeting, Orthopaedic Research Society, Mar. 12-15, 2000, Orlando, Florida, Jan. 1, 2010, p. 450; 1 pages.
D. A. Simon; R. V. O'Toole; M. Blackwell; F. Morgan; A. M. Digioia; T. Kanade, Accuracy validation in image-guided orthopaedic surgery, In Medical Robotics and Computer Assisted Surgery, 1995, pp. 185-192, Wiley; 8 pages.
B.L. Davies; K.L. Fan; R.D. Hibberd; M. Jakopec; S.J. Harris, Acrobot—using robots and surgeons synergistically in knee surgery, Advanced Robotics, 1997. ICAR '97. Proceedings., 8th International Conference on, Jul. 7-9, 1997, pp. 173-178, IEEE,Monterey, CA, USA; 6 pages.
B.L. Davies; S.J. Harris; W.J. Lin; R.D. Hibberd; R. Middleton; J.C. Cobb, Active compliance in robotic surgery—the use of force control as a dynamic constraint, Proceedings of the Institution of Mechanical Engineers, Part H: Journal of Engineeringin Medicine, Apr. 1, 1997, pp. 285-292, vol. 211, Sage; 9 pages.
J. K. Salisbury, Active Stiffness Control of a Manipulator in Cartesian Coordinates, Decision and Control including the Symposium on Adaptive Processes, 1980 19th IEEE Conference on, Dec. 1980, pp. 95-100, vol. 19, IEEE, Stanford, CA, USA; 7 pages.
O. Tonet; G. Megali; S. D'Attanasio; P. Dario; M. C. Carrozza; M. Marcacci; S. Marta; P. F. La Palombara, An Augmented Reality Navigation System for Computer Assisted Arthroscopic Surgery of the Knee, Medical Image Computing and Computer-Assisted Intervention—MICCAI 2000, Lecture Notes in Computer Science, 2000, pp. 1158-1162, vol. 1935, Springer Berlin Heidelberg; 5 pages.
R.H. Taylor; H. A. Paul; B.D. Mittelstadt; W. Hanson; P. Kazanzides; J. Zuhars; E. Glassman; B.L. Mustis; B. Williamson; W.L. Bargar, An Image-directed Robotic System for Hip Replacement Surgery, Oct. 1990, pp. 111-116, vol. 8, No. 5; 7 pages.
R.H. Taylor; B.D. Mittelstadt; H.A. Paul; W. Hanson; P. Kazanzides; J.F. Zuhars; B. Williamson; B.L. Musits; E. Glassman; W.L. Bargar, An Image-Directed Robotic System for Precise Orthopaedic Surgery, Robotics and Automation, IEEE Transactions on,Jun. 1994, pp. 261-275, vol. 10, Issue 3, IEEE; 15 pages.
T.C. Kienzle, III; S.D. Stulberg; M. Peshkin; A. Quaid; C.-H. Wu, An Integrated CAD-Robotics System for Total Knee Replacement Surgery, Systems, Man and Cybernetics, 1992., IEEE International Conference on, Oct. 18-21, 1992, pp. 1609-1614, vol. 2,IEEE, Chicago, IL, USA; 6 pages.
P. Kazanzides; J. Zuhars; B. Mittelstadt; B. Williamson; P. Cain; F. Smith; L. Rose; B. Musits, Architecture of a Surgical Robot, Systems, Man and Cybernetics, 1992., IEEE International Conference on, Oct. 18-21, 1992, pp. 1624-1629, vol. 2, IEEE,Chicago, IL, USA; 6 pages.
K. Hyosig; J.T. Wen, Autonomous Suturing using Minimally Invasive Surgical Robots, Control Applications, Sep. 25-27, 2000. Proceedings of the 2000 IEEE International Conference on, 2000, pp. 742-747, IEEE, Anchorage, AK, USA; 6 pages. cited byapplicant.
R.V. O'Toole, III; B. Jaramaz; A.M. Digioia, III; C.D. Visnic; R.H. Reid, Biomechanics for Preoperative Planning and Surgical Simulations in Orthopaedics, Computers in Biology and Medicine, Mar. 1995, pp. 183-191, vol. 25, Issue 2; 8 pages. cited byapplicant.
C.O.R. Grueneis; R.J. Richter; F.F. Hennig, Clinical Introduction of the Caspar System Problems and Initial Results, 4th International Symposium of Computer Assited Orthopaedic Surgery, CAOS'99, Abstracts from CAOS '99, 1999, p. 160, Davos,Switzerland; 1 pages.

(56) References Cited

OTHER PUBLICATIONS

R. Khadem; C.C. Yeh; M.Sadeghi-Tehrani; M.R. Bax; J.A. Johnson; J.L. Welch; E.P. Wilkinson; R. Shahidi, Comparative Tracking Error Analysis of Five Different Optical Tracking Systems, Computer Aided Surgery, 2000, pp. 98-107, vol. 5, Stanford, CA,USA; 10 pages.
R. Rohling; P. Munger; J.M. Hollerbach; T. Peter, Comparison of Relative Accuracy Between a Mechanical and an Optical Position Tracker for Image-Guided Neurosurgery, Journal of Image Guided Surgery, 1995, pp. 30-34, vol. 1, No. 1; 4 pages. cited byapplicant.
S.L. Delp; S. D. Stulberg; B. Davies; F. Picard; F. Leitner, Computer Assisted Knee Replacement, Clinical Orthopaedics, Sep. 1998, pp. 49-56, vol. 354, Lippincott-Raven Publishers; 8 pages.
A.M. Digioia, III; B. Jaramaz; B. D. Colgan, Computer Assisted Orthopaedic Surgery Image Guided and Robotic Assistive Technologies, Clinical Orthopaedics & Related Research:. Sep. 1998, pp. 8-16, vol. 354, Lippincott Williams & Wilkins, Pittsburgh,PA, USA; 9 pages.
M. Fadda, D. Bertelli, S. Martelli, M. Marcacci, P. Dario, C. Paggetti, D. Caramella and D. Trippi, Computer Assisted Planning for Total Knee Arthroplasty, 1997, pp. 619-628; 10 pages.
S. Lavallee, P. Sautot, J. Troccaz P. Cinquin and P. Merloz, Computer Assisted Spine Surgery a technique for accurate transpedicular screw fixation using CT data and a 3-D optical localizer, Journal of Image Guided Surgery, 1995, pp. 65-73; 9 pages.
B. Davies, Computer-assisted and robotics surgery, International Congress and Symposium Series 223, 1997, pp. 71-82, Royal Society of Medicine Press Limited; 12 pages.
M. Fadda, T. Wang, M. Marcacci, S. Martelli, P. Dario, G. Marcenaro, M. Nanetti, C. Paggetti, A. Visani and S. Zaffagnini, Computer-Assisted Knee Arthroplasty at Rizzoli Institutes, First International Symposium on Medical Robotics and ComputerAssisted Surgery, Sep. 22-24, 1994, pp. 26-30, Pittsburgh, Pennsylvania, US; 6 pages.
F. Leitner, F. Picard, R. Minfelde, H.-J. Schulz, P. Cinquin and S. Saragaglia, Computer-Assisted Knee Surgical Total Replacement, CVRMed-MRCAS'97, Lecture Notes in Computer Science vol. 1205, 1997, pp. 629-638, Springer Berlin Heidelberg, Jan. 1, 1997; 10 pages.
E. Bainville, I. Bricault, P. Cinquin and S. Lavall'ee, Concepts and Methods of Registration for Computer-Integrated Surgery, Computer Assisted Orthopedic Surgery (CAOS), 1999, pp. 15-34, Hogrefe & Huber Publishers, Bern; 22 pages. cited byapplicant.
G. Brandt, A. Zimolong, L. Carrat, P. Merloz, H.-W. Staudte, S. Lavallee, K. Radermacher, G. Rau, "CRIGOS: A Compact Robot for Image-Guided Orthopedic Surgery," Information Technology in Biomedicine, IEEE Transactions on, vol. 3, No. 4, pp. 252-260,Dec. 1999; 9 pages.
Y. Louhisalmi; T. Leinonen, Development of a Robotic Surgical Assistant, 1994, pp. 1043-1044, IEEE, Linnanmaa, Oulu, FL; 2 pages.
H.A. Paul; W.L. Bargar; B. Mittlestadt; B. Musits; R. H. Taylor; P. Kazanzides; J. Zuhars; B. Williamson; W. Hanson, Development of a Surgical Robot for Cementless Total Hip Arthroplasty, Clinical Orthopaedics and Related Research, Dec. 1992, pp. 57-66, No. 285, Sacramento, CA, USA; 10 pages.
R. Abovitz, Digital surgery the future of medicine and human-robot symbiotic interaction, Industrial Robot: An International Journal, 2001, pp. 401-406, vol. 28, Issue 5, Hollywood, FL, USA; 5 pages.
T. Schmidt; W. Hentschel, EasyGuide Neuro, A New System for Image-Guided Planning, Simulation and Navigation in Neurosurgery, Biomedical Engineering, vol. 40, Supplement 1, 1995, pp. 233-234, Hamburg, DE; 2 pages.
J. Raczkowsky; J. Munchenberg; I. Bertovic; C. Burghart, Ein Robotersystem fur craniomaxillofaciale chirurgische Eingriffe (A robotic system for surgical procedures craniomaxillofaciale), Computer Forsch. Entw., 1999, pp. 24-35, vol. 14,Springer-Verlag; 12 pages.
K. Hyosig; J.T. Wen, EndoBot A Robotic Assistant in Minimally Invasive Surgeries, Robotics and Automation, 2001. Proceedings 2001 ICRA. IEEE International Conference on, Seoul, KR, 2001, pp. 2031-2036, vol. 2, IEEE, Troy, NY, USA; 6 pages. cited byapplicant.
S. J. Hams; W. J. Lin; K. L. Fan; R. D. Hibberd; J. Cobb; R. Middleton; B. L. Davies, Experiences with Robotic Systems for Knee Surgery, CVRMed-MRCAS'97, Lecture Notes in Computer Science, 1997, pp. 757-766, vol. 1205, Springer Berlin Heidelberg,London, UK; 10 pages.
D. Y. Choi and C. N. Riviere, Flexure-based Manipulator for Active Handheld Microsurgical Instrument, Engineering in Medicine and Biology Society, 2005. Proceedings of the 2005 IEEE Engineering in Medicine and Biology 27th Annual Conference of theDigital Object Identifier, 2005, pp. 5085-5088, IEEE, Shanghai, China, Sep. 1-4, 2005; 4 pages.
S.C. Ho; R.D. Hibberd; J. Cobb; B.L. Davies, Force Control for Robotic Surgery, ICAR '95, 1995, pp. 21-32, London, UK; 12 pages.
U. Spetzger; G. Laborde; J.M. Gilsbach, Frameless Neuronavigation in Modern Neurosurgery, Minimally Invasive Neurosurgery, Dec. 1995, pp. 163-166, vol. 38; 4 pages.
J. Troccaz, M. Peshkin and B. Davies, Guiding systems for computer-assisted surgery introducing synergistic devices and discussing the different approaches, Medical Image Analysis, Jun. 1998, vol. 2, No. 2, pp. 101-119, Elsevier B.V.; 19 pages.
A.E. Quaid, III; R.A. Abovitz, Haptic Information Displays for Computer-Assisted Surgery, Robotics and Automation, 2002 Proceedings. ICRA '02. IEEE International Conference on, May 2002, pp. 2092-2097, vol. 2, IEEE, Washington DC, USA; 6 pages.
R.A. Abovitz, Human-Interactive Medical Robotics, Abstract for CAOS 2000, 2000, pp. 71-72; 2 pages.
English language abstract and machine-assisted English translation for KR 2010-0098055 extracted from espacenet.com database on Jun. 27, 2019, 14 pages.
English language abstract and machine-assisted English translation for KR 2011-0036453 extracted from espacenet.com database on Jun. 27, 2019, 31 pages.

\* cited by examiner

SYSTEMS AND METHODS FOR ESTABLISHING VIRTUAL CONSTRAINT BOUNDARIES

RELATED APPLICATIONS

This application is a divisional of U.S. patent application Ser. No. 14/205,702 filed on Mar. 12, 2014, which claims the benefit of U.S. provisional patent application No. 61/780,148, filed on Mar. 13, 2013, the advantages and disclosures of the above-referenced applications are hereby incorporated by reference in their entirety.

TECHNICAL FIELD

The present invention relates generally to systems and methods for establishing and tracking virtual boundaries.

BACKGROUND

In robotic surgery virtual boundaries are created using computer aided design software to delineate areas in which an end effector of a robotic system can maneuver from areas in which the end effector is restricted. For instance, in orthopedic surgery a virtual cutting boundary may be created to delineate sections of bone to be removed by the end effector during the surgery from sections of bone that are to remain after the surgery.

A navigation system tracks movement of the end effector with respect to the virtual cutting boundary to determine a position and/or orientation of the end effector relative to the virtual cutting boundary. The robotic system cooperates with the navigation system to guide movement of the end effector so that the end effector does not move beyond the virtual cutting boundary.

Typically, virtual cutting boundaries are created prior to surgery. Virtual cutting boundaries are often created in a model of a patient's bone and fixed with respect to the bone so that when the model is loaded into the navigation system, the navigation system can track movement of the virtual cutting boundary by tracking movement of the bone.

Virtual boundaries may define other anatomical features to be avoided by the end effector during surgery. Such features include nerves or other types of tissue to be protected from contact with the end effector. Virtual boundaries are also used to provide virtual pathways that direct the end effector toward the anatomy being treated. These examples of virtual boundaries are often fixed in relationship to the anatomy being treated so that all of the boundaries are tracked together as the anatomy moves. However, some anatomical features or other objects in the operating room may move relative to the anatomy being treated. For instance, retractors used to provide an opening in tissue for the end effector may move relative to the anatomy being treated. If not accurately tracked using an appropriate dynamic virtual constraint boundary, the end effector may inadvertently strike the retractors. As a result, the end effector may be damaged or become inoperative and the retractor may become dislodged from its position.

Other typically untracked objects may also be in proximity to the end effector that should be avoided by the end effector, yet move relative to the anatomy being treated. Therefore, there is a need in the art for systems and methods for creating dynamic virtual boundaries for such objects.

SUMMARY

In one embodiment a system is provided that uses a plurality of dynamic virtual boundaries to guide movement of an instrument. The system includes an instrument tracking device to track movement of the instrument. The system also includes a first boundary tracking device to track movement of a first of the plurality of virtual boundaries wherein the first virtual boundary is associated with the anatomy to be treated. The system further includes a second boundary tracking device to track movements of a second of the plurality of virtual boundaries wherein the second virtual boundary is associated with an object to be avoided by the instrument. A controller is configured to receive information associated with the tracking devices including positions of the instrument relative to the first and second virtual boundaries. The controller is configured to guide movement of the instrument relative to each of the first and second virtual boundaries as the first and second virtual boundaries move relative to one another.

In another embodiment a method is provided for using a plurality of dynamic virtual boundaries to guide movement of an instrument. The method includes tracking movement of the instrument and a first virtual boundary associated with the anatomy to be treated. The method further includes tracking movement of a second virtual boundary relative to the first virtual boundary wherein the second virtual boundary is associated with an object to be avoided by the instrument. Movement of the instrument is guided relative to each of the first and second virtual boundaries as the first and second virtual boundaries move relative to one another.

One advantage of these embodiments is the ability to dynamically track objects (such as other tools or anatomy) that may move relative to the anatomy of interest, in addition to tracking the instrument. The second virtual boundary can be a virtual constraint boundary or other type of virtual boundary that is tracked for movement relative to the first virtual boundary associated with the anatomy.

BRIEF DESCRIPTION OF THE DRAWINGS

Advantages of the present invention will be readily appreciated as the same becomes better understood by reference to the following detailed description when considered in connection with the accompanying drawings wherein.

DETAILED DESCRIPTION

Figure 1:
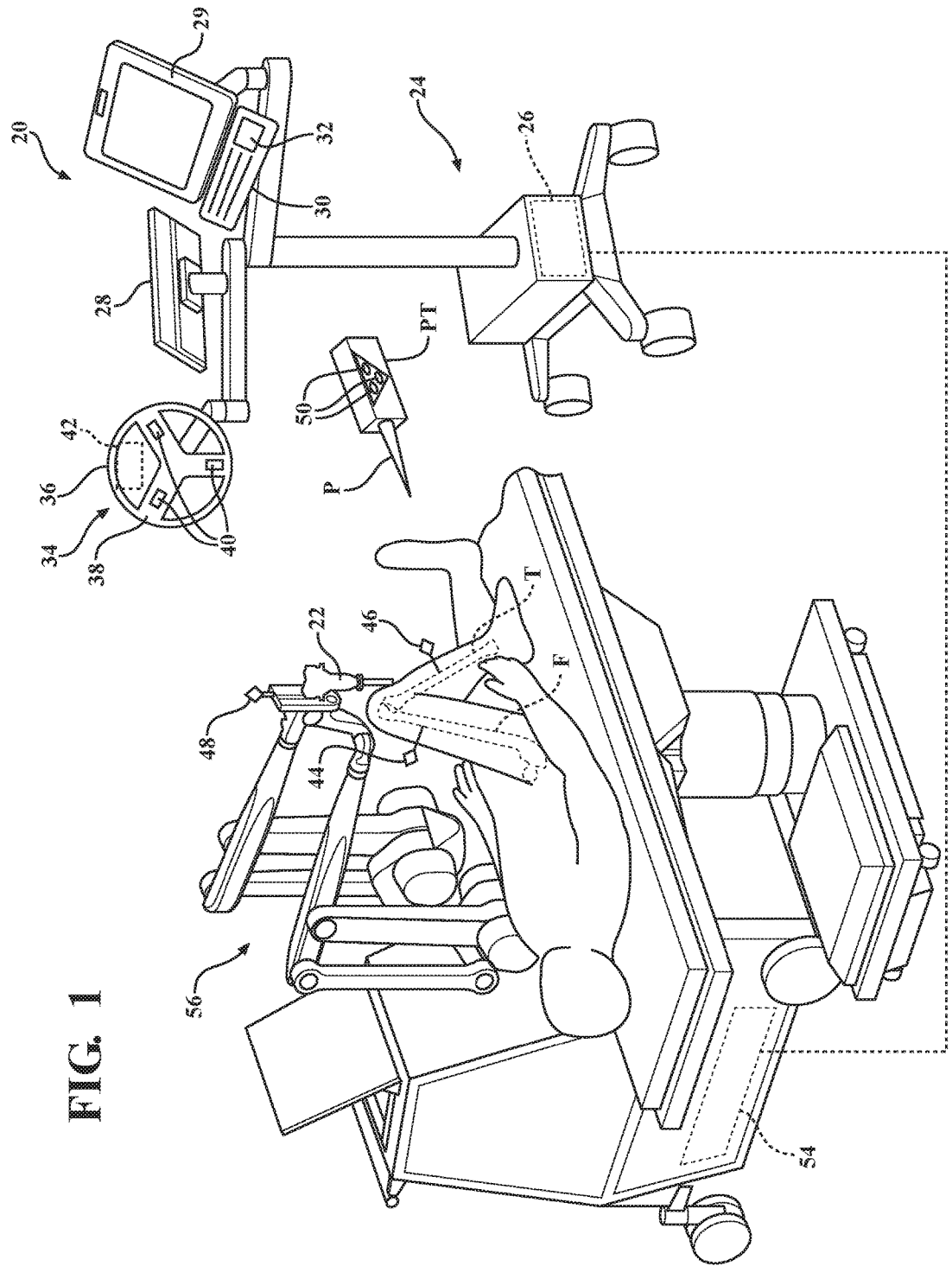
FIG. 1 is a perspective view of a navigation system of the present invention being used in conjunction with a robotic system.

Referring to FIG. 1 a surgical navigation system 20 is illustrated. The system 20 is shown in a surgical setting such as an operating room of a medical facility. The navigation system 20 is set up to track movement of various objects in the operating room. Such objects include, for example, a surgical instrument 22, a femur F of a patient, and a tibia T of the patient. The navigation system 20 tracks these objects for purposes of displaying their relative positions and orientations to the surgeon and, in some cases, for purposes of controlling or constraining movement of the surgical instrument 22 relative to virtual cutting boundaries associated with the femur F and tibia T.

The surgical navigation system 20 includes a computer cart assembly 24 that houses a navigation computer 26. A navigation interface is in operative communication with the navigation computer 26. The navigation interface includes a first display 28 adapted to be situated outside of the sterile field and a second display 29 adapted to be situated inside the sterile field. The displays 28, 29 are adjustably mounted to the computer cart assembly 24. First and second input devices 30, 32 such as a keyboard and mouse can be used to input information into the navigation computer 26 or otherwise select/control certain aspects of the navigation computer 26. Other input devices are contemplated including a touch screen (not shown) or voice-activation.

A localizer 34 communicates with the navigation computer 26. In the embodiment shown, the localizer 34 is an optical localizer and includes a camera unit 36 (one example of a sensing device). The camera unit 36 has an outer casing 38 that houses one or more optical position sensors 40. In some embodiments at least two optical sensors 40 are employed, preferably three. The optical sensors 40 may be three separate charge-coupled devices (CCD). In one embodiment three, one-dimensional CCDs are employed. It should be appreciated that in other embodiments, separate camera units, each with a separate CCD, or two or more CCDs, could also be arranged around the operating room. The CCDs detect infrared (IR) signals.

Camera unit 36 is mounted on an adjustable arm to position the optical sensors 40 with a field of view of the below discussed trackers that, ideally, is free from obstructions. In some embodiments the camera unit 36 is adjustable in at least one degree of freedom by rotating about a rotational joint. In other embodiments, the camera unit 36 is adjustable about two or more degrees of freedom.

The camera unit 36 includes a camera controller 42 in communication with the optical sensors 40 to receive signals from the optical sensors 40. The camera controller 42 communicates with the navigation computer 26 through either a wired or wireless connection (not shown). One such connection may be an IEEE 1394 interface, which is a serial bus interface standard for high-speed communications and isochronous real-time data transfer. The connection could also use a company specific protocol. In other embodiments, the optical sensors 40 communicate directly with the navigation computer 26.

Position and orientation signals and/or data are transmitted to the navigation computer 26 for purposes of tracking objects. The computer cart assembly 24, display 28, and camera unit 36 may be like those described in U.S. Pat. No. 7,725,162 to Malackowski, et al. issued on May 25, 2010, entitled "Surgery System", hereby incorporated by reference.

The navigation computer 26 can be a personal computer or laptop computer. Navigation computer 26 has the display 28, central processing unit (CPU) and/or other processors, memory (not shown), and storage (not shown). The navigation computer 26 is loaded with software as described below. The software converts the signals received from the camera unit 36 into data representative of the position and orientation of the objects being tracked.

Navigation system 20 includes a plurality of tracking devices 44, 46, 48, also referred to herein as trackers. In the illustrated embodiment, one tracker 44 is firmly affixed to the femur F of the patient and another tracker 46 is firmly affixed to the tibia T of the patient. Trackers 44, 46 are firmly affixed to sections of bone. Trackers 44, 46 may be attached to the femur F and tibia T in the manner shown in U.S. Pat. No. 7,725,162, hereby incorporated by reference. Trackers 44, 46 could also be mounted like those shown in U.S. Provisional Patent Application No. 61/753,219, filed on Jan. 16, 2013, entitled, "Tracking Devices and Navigation Systems and Methods for Use Thereof", hereby incorporated by reference herein. In additional embodiments, a tracker (not shown) is attached to the patella to track a position and orientation of the patella. In yet further embodiments, the trackers 44, 46 could be mounted to other tissue types or parts of the anatomy.

An instrument tracker 48 is firmly attached to the surgical instrument 22. The instrument tracker 48 may be integrated into the surgical instrument 22 during manufacture or may be separately mounted to the surgical instrument 22 in preparation for the surgical procedures. The working end of the surgical instrument 22, which is being tracked by virtue of the instrument tracker 48, may be a rotating bur, electrical ablation device, or the like.

The trackers 44, 46, 48 can be battery powered with an internal battery or may have leads to receive power through the navigation computer 26, which, like the camera unit 36, preferably receives external power.

In the embodiment shown, the surgical instrument 22 is attached to a surgical manipulator. Such an arrangement is shown in U.S. patent application Ser. No. 13/958,070, entitled, "Surgical Manipulator Capable of Controlling a Surgical Instrument in Multiple Modes", the disclosure of which is hereby incorporated by reference.

In other embodiments, the surgical instrument 22 may be manually positioned by only the hand of the user, without the aid of any cutting guide, jig, or other constraining mechanism such as a manipulator or robot. Such a surgical instrument is described in U.S. patent application Ser. No. 13/600,888, filed Aug. 31, 2012, entitled, "Surgical Instrument Including Housing, a Cutting Accessory that Extends from the Housing and Actuators that Establish the Position of the Cutting Accessory Relative to the Housing", hereby incorporated by reference.

The optical sensors 40 of the localizer 34 receive light signals from the trackers 44, 46, 48. In the illustrated embodiment, the trackers 44, 46, 48 are active trackers. In this embodiment, each tracker 44, 46, 48 has at least three active tracking elements or markers for transmitting light signals to the optical sensors 40. The active markers can be, for example, light emitting diodes or LEDs 50 transmitting light, such as infrared light. The optical sensors 40 preferably have sampling rates of 100 Hz or more, more preferably 300 Hz or more, and most preferably 500 Hz or more. In some embodiments, the optical sensors 40 have sampling rates of 8000 Hz. The sampling rate is the rate at which the optical sensors 40 receive light signals from sequentially fired LEDs 50. In some embodiments, the light signals from the LEDs 50 are fired at different rates for each tracker 44, 46, 48.

Figure 2:
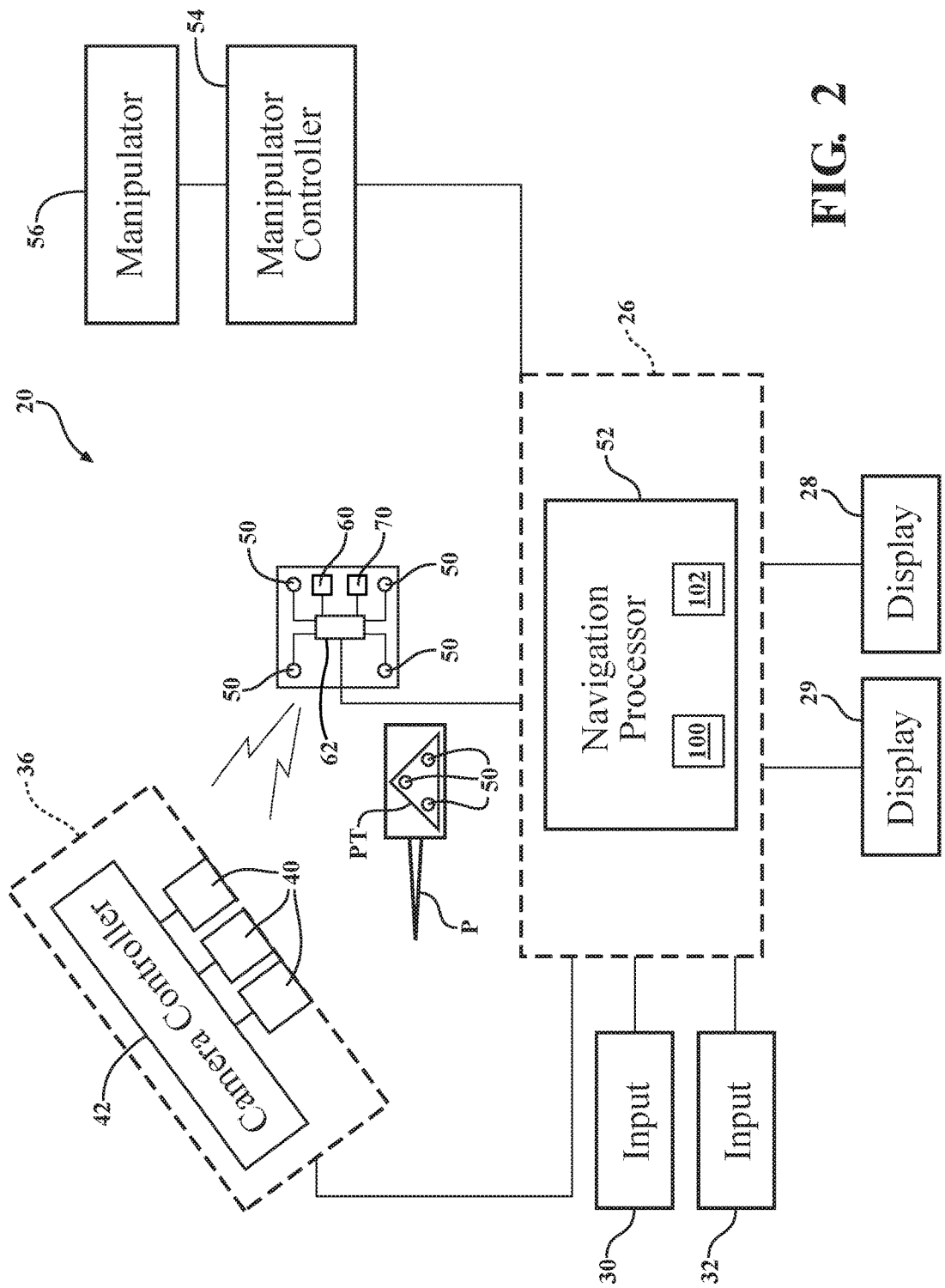
FIG. 2 is a schematic view of the navigation system.

Referring to FIG. 2, each of the LEDs 50 are connected to a tracker controller 62 located in a housing (not shown) of the associated tracker 44, 46, 48 that transmits/receives data to/from the navigation computer 26. In one embodiment, the tracker controllers 62 transmit data on the order of several Megabytes/second through wired connections with the navigation computer 26. In other embodiments, a wireless connection may be used. In these embodiments, the navigation computer 26 has a transceiver (not shown) to receive the data from the tracker controller 62.

In other embodiments, the trackers 44, 46, 48 may have passive markers (not shown), such as reflectors that reflect light emitted from the camera unit 36. The reflected light is then received by the optical sensors 40. Active and passive arrangements are well known in the art.

In some embodiments, the trackers 44, 46, 48 also include a gyroscope sensor 60 and accelerometer 70, such as the trackers shown in U.S. Provisional Patent Application No. 61/753,219, filed on Jan. 16, 2013, entitled, "Tracking Devices and Navigation Systems and Methods for Use Thereof", hereby incorporated by reference.

The navigation computer 26 includes a navigation processor 52. It should be understood that the navigation processor 52 could include one or more processors to control operation of the navigation computer 26. The processors can be any type of microprocessor or multi-processor system. The term processor is not intended to limit the scope of the invention to a single processor.

The camera unit 36 receives optical signals from the LEDs 50 of the trackers 44, 46, 48 and outputs to the processor 52 signals relating to the position of the LEDs 50 of the trackers 44, 46, 48 relative to the localizer 34. Based on the received optical (and non-optical signals in some embodiments), navigation processor 52 generates data indicating the relative positions and orientations of the trackers 44, 46, 48 relative to the localizer 34.

Prior to the start of the surgical procedure, additional data are loaded into the navigation processor 52. Based on the position and orientation of the trackers 44, 46, 48 and the previously loaded data, navigation processor 52 determines the position of the working end of the surgical instrument 22 and the orientation of the surgical instrument 22 relative to the tissue against which the working end is to be applied. In some embodiments, navigation processor 52 forwards these data to a manipulator controller 54. The manipulator controller 54 can then use the data to control a robotic manipulator 56 as described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference.

The navigation processor 52 also generates image signals that indicate the relative position of the surgical instrument working end to the tissue. These image signals are applied to the displays 28, 29. Displays 28, 29, based on these signals, generate images that allow the surgeon and staff to view the relative position of the surgical instrument working end to the surgical site. The displays, 28, 29, as discussed above, may include a touch screen or other input/output device that allows entry of commands.

Figure 3:
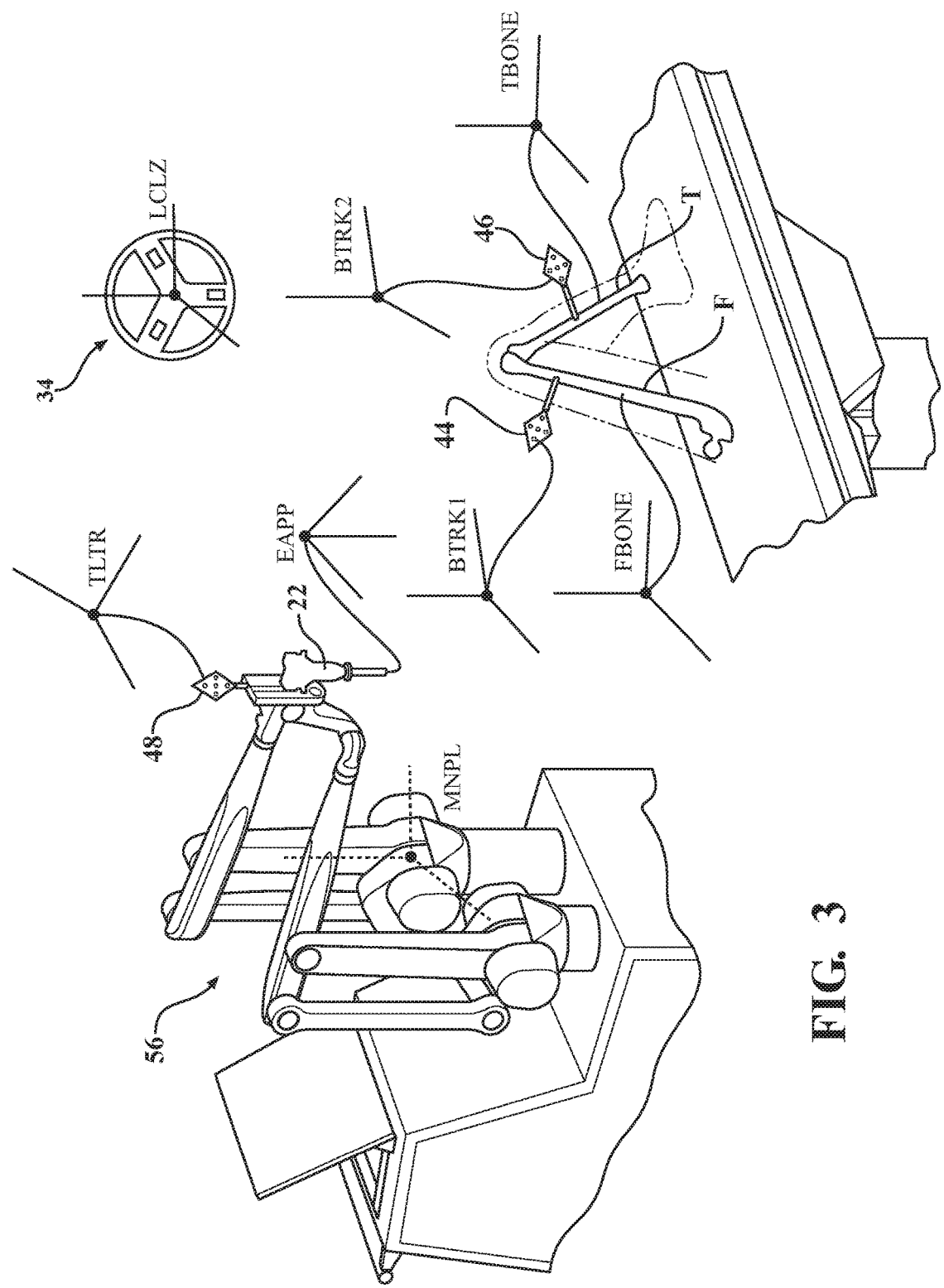
FIG. 3 is schematic view of the coordinate systems used in the navigation system.

Referring to FIG. 3, tracking of objects is generally conducted with reference to a localizer coordinate system LCLZ. The localizer coordinate system has an origin and an orientation (a set of x-, y-, and z-axes). During the procedure one goal is to keep the localizer coordinate system LCLZ in a known position. An accelerometer (not shown) mounted to the camera unit 36 may be used to track sudden or unexpected movement of the localizer coordinate system LCLZ, as may occur when the camera unit 36 is inadvertently bumped by surgical personnel.

Each tracker 44, 46, 48 and object being tracked also has its own coordinate system separate from localizer coordinate system LCLZ. Components of the navigation system 20 that have their own coordinate systems are the bone trackers 44, 46 and the instrument tracker 48. These coordinate systems are represented as, respectively, bone tracker coordinate systems BTRK1, BTRK2, and instrument tracker coordinate system TLTR.

Navigation system 20 monitors the positions of the femur F and tibia T of the patient by monitoring the position of bone trackers 44, 46 firmly attached to bone. Femur coordinate system is FBONE and tibia coordinate system is TBONE, which are the coordinate systems of the bones to which the bone trackers 44, 46 are firmly attached.

Prior to the start of the procedure, pre-operative images of the femur F and tibia T are generated (or of other tissues in other embodiments). These images may be based on MRI scans, radiological scans or computed tomography (CT) scans of the patient's anatomy. These images are mapped to the femur coordinate system FBONE and tibia coordinate system TBONE using well known methods in the art. These images are fixed in the femur coordinate system FBONE and tibia coordinate system TBONE. As an alternative to taking pre-operative images, plans for treatment can be developed in the operating room (OR) from kinematic studies, bone tracing, and other methods.

During an initial phase of the procedure, the bone trackers 44, 46 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIGS. 1 and 2), such as disclosed in U.S. Pat. No. 7,725,162 to Malackowski, et al., hereby incorporated by reference, having its own tracker PT (see FIG. 2), may be used to register the femur coordinate system FBONE and tibia coordinate system TBONE to the bone tracker coordinate systems BTRK1 and BTRK2, respectively. Given the fixed relationship between the bones and their bone trackers 44, 46, positions and orientations of the femur F and tibia T in the femur coordinate system FBONE and tibia coordinate system TBONE can be transformed to the bone tracker coordinate systems BTRK1 and BTRK2 so the camera unit 36 is able to track the femur F and tibia T by tracking the bone trackers 44, 46. This pose-describing data are stored in memory integral with both manipulator controller 54 and navigation processor 52.

The working end of the surgical instrument 22 (also referred to as energy applicator distal end) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with both manipulator controller 54 and navigation processor 52.

Referring to FIG. 2, a localization engine 100 is a software module that can be considered part of the navigation system 20. Components of the localization engine 100 run on navigation processor 52. In some versions of the invention, the localization engine 100 may run on the manipulator controller 54.

Localization engine 100 receives as inputs the optically-based signals from the camera controller 42 and, in some embodiments, the non-optically based signals from the tracker controller 62. Based on these signals, localization engine 100 determines the pose of the bone tracker coordinate systems BTRK1 and BTRK2 in the localizer coordinate system LCLZ. Based on the same signals received for the instrument tracker 48, the localization engine 100 determines the pose of the instrument tracker coordinate system TLTR in the localizer coordinate system LCLZ.

The localization engine 100 forwards the signals representative of the poses of trackers 44, 46, 48 to a coordinate transformer 102. Coordinate transformer 102 is a navigation system software module that runs on navigation processor 52. Coordinate transformer 102 references the data that defines the relationship between the pre-operative images of the patient and the bone trackers 44, 46. Coordinate transformer 102 also stores the data indicating the pose of the working end of the surgical instrument relative to the instrument tracker 48.

During the procedure, the coordinate transformer 102 receives the data indicating the relative poses of the trackers 44, 46, 48 to the localizer 34. Based on these data and the previously loaded data, the coordinate transformer 102 generates data indicating the relative position and orientation of both the coordinate system EAPP, and the bone coordinate systems, FBONE and TBONE to the localizer coordinate system LCLZ.

As a result, coordinate transformer 102 generates data indicating the position and orientation of the working end of the surgical instrument 22 relative to the tissue (e.g., bone) against which the instrument working end is applied. Image signals representative of these data are forwarded to displays 28, 29 enabling the surgeon and staff to view this information. In certain embodiments, other signals representative of these data can be forwarded to the manipulator controller 54 to guide the manipulator 56 and corresponding movement of the surgical instrument 22.

Before using the surgical instrument 22 to treat the patient, certain preparations are necessary such as draping the patient and preparing the surgical site for treatment. For instance, in knee arthroplasty, surgical personnel may secure the leg of interest in a leg holder, and drape the patient and equipment. One such leg holder is shown in U.S. patent application Ser. No. 13/554,010, entitled, "Multi-position Limb Holder", published as U.S. Patent Application Publication No. 2013/0019883, hereby incorporated by reference.

Other preparations include placing objects needed for surgery in the operating room. Some of these objects are used in proximity to areas in which the surgical instrument 22 will maneuver. These objects can include leg holders, retractors, suction/irrigation tools, surgical personnel, and the like. During the surgery, these objects are to be avoided by the surgical instrument 22. To facilitate the avoidance of these objects during the surgery position information for one or more of these objects is determined either directly or indirectly. In some embodiments, one or more of the objects are dynamically tracked by the navigation system 20 during the surgery.

Figure 4:
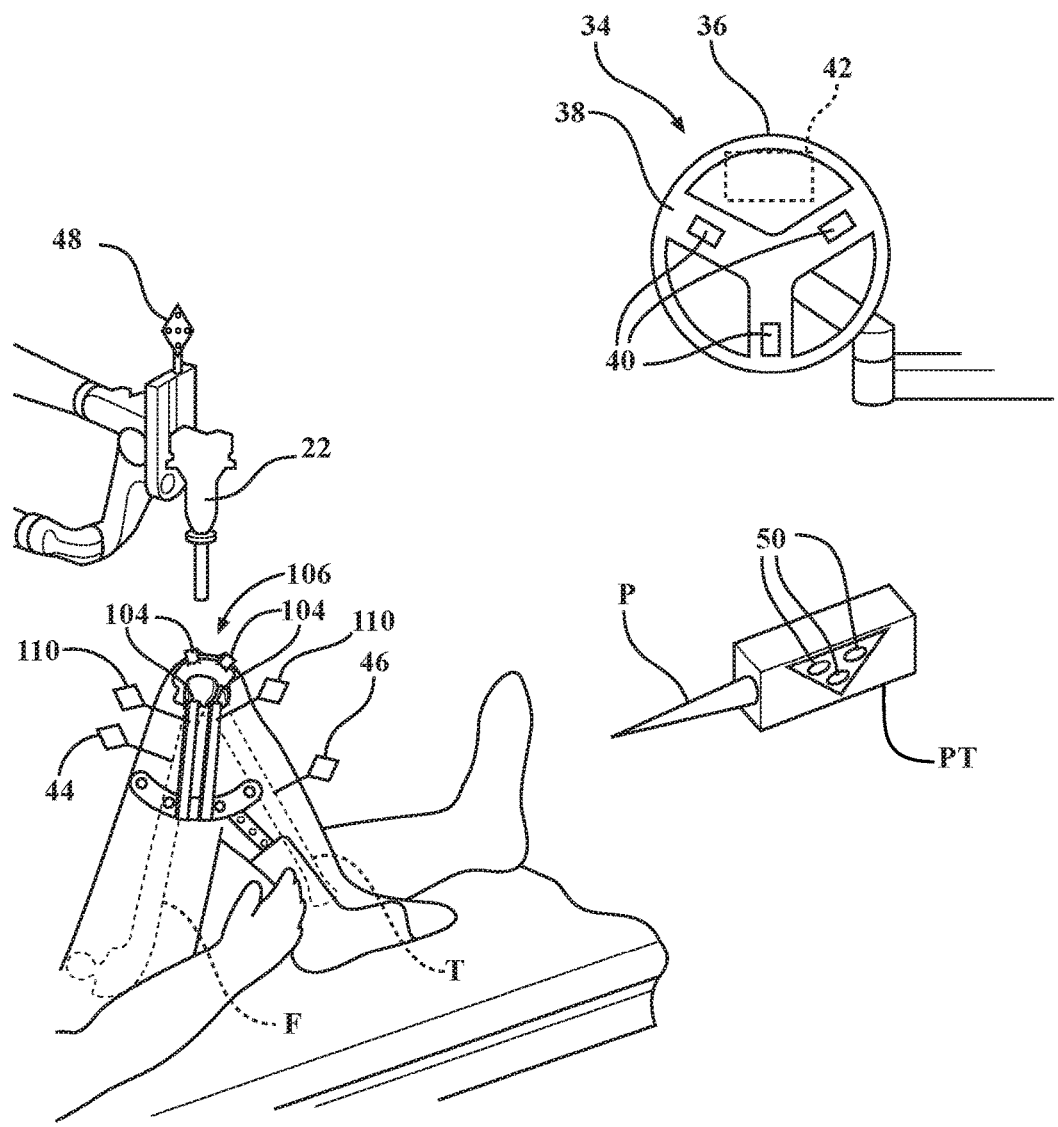
FIG. 4 is a perspective view of a tissue opening for accessing a knee joint by an end effector of the robotic system.

Referring to FIG. 4, in one embodiment, position information can be obtained indirectly from an object using the pointer instrument P, an example of which is disclosed in U.S. Pat. No. 7,725,162 to Malackowski, et al., hereby incorporated by reference. The pointer P has its own tracker PT with LEDs 50 that transmit signals to the camera unit 36 in the same manner as trackers 44, 46, 48. Position of a tip of the pointer P is known relative to the LEDs 50 on the pointer P and stored in the pointer P in electronic format for later transmitting to the camera unit 36 via transceivers. Alternatively, the position information for the tip is stored in the navigation computer 26 or calibrated to a known location in the field. In either case, since the tip position is known, the pointer P can be used to determine the positions of objects to be avoided by the surgical instrument 22.

Once the tip touches certain surfaces of the object, a trigger or switch (not shown) on the pointer P is actuated by the user or alternatively the tip may include a sensor that automatically senses when it is in contact with a surface. A corresponding signal is sent to the transceiver on the camera unit 36 to read the signals from the LEDs 50 on the pointer tracker PT so that the position of the tip can be calculated, which correlates to a point on the surface of the object. As more points on the surface are touched by the tip and their positions calculated by the navigation system 20, models of the object can be created to define a position and orientation of the object in the localizer coordinate system LCLZ. Such models can be created using conventional surface mapping tools and the like.

The created models are used as virtual constraint boundaries to guide movement of the surgical instrument 22. The models may be displayed on displays 28, 29 to show the locations of the objects and/or information relating to the models can be forwarded to the manipulator controller 54 to guide the manipulator 56 and corresponding movement of the surgical instrument 22 relative to these virtual constraint boundaries to prevent the object from being contacted by the surgical instrument 22.

When the object is stationary during the surgery the above method of determining position and/or orientation is suitable to provide a virtual constraint boundary, or if the object to be tracked is not stationary, but in a fixed location relative to another tracked object. However, if the object typically moves during the surgery, additional measures are needed to enable continuous tracking of the object. In some embodiments, mountable trackers 110 may be mounted to the objects. These trackers 110 may be generic with respect to the objects and thus, not be calibrated to the objects. In this case, the trackers 110 are first attached to the objects.

One such object may be a retractor, such as the retractor assemblies 104 shown in FIG. 4. The trackers 110 may be attached to the retractor assemblies 104 by a tracker connector located on the retractor assemblies 104, such as those shown in U.S. Pat. No. 7,725,162 to Malackowski, et al., hereby incorporated by reference, or the trackers 110 may be mounted with conventional fasteners or clamps to fix the trackers 110 to the retractor assemblies 104. Examples of retractor assemblies that may be used are shown in U.S. patent application Ser. No. 13/554,010, entitled, "Multi-position Limb Holder", published as U.S. Patent Application Publication No. 2013/0019883, hereby incorporated by reference. Once the tracker 110 is fixed to the retractor assembly 104, the pointer P can be used to register the surfaces or other points on the retractor assembly 104. Each tracker 110 includes three or more LEDs (not shown) that transmit signals to the camera unit 36 in the same manner as trackers 44, 46, 48. The camera unit 36 and/or navigation computer 26 are then able to determine a position of each of the LEDs in the localizer coordinate system LCLZ. While the camera unit 36 is receiving signals from the LEDs on tracker 110, the pointer P is used to touch on several points on the retractor assembly 104 and transmit corresponding signals to the camera unit 36 to determine position information from the pointer P using the pointer tracker PT. This enables the navigation computer 26 to associate points on the retractor assembly 104 with positions of the LEDs on the tracker 110. Then, through a boundary creation software module (not shown) run by the navigation processor 52, a virtual constraint boundary can be created that is associated with the retractor assembly 104 and dynamically trackable via the tracker 110.

In some embodiments, the boundary can be created by connecting each of the captured points together. This creates a web or mesh that defines a surface boundary. If only two points are captured, the boundary may be a line between the points. If three points are captured, the boundary may be a triangle formed by lines connecting adjacent points. The displays 28, 29 can be used to provide visual feedback of the shape of the boundary created. The input devices, e.g., mouse, touch screen, etc. could be used to modify the boundary such as by shifting the boundary, enlarging or shrinking the boundary, changing the shape of the boundary, etc. Once created, the boundary may be defined in the boundary creation software module as a virtual constraint boundary across which the surgical instrument 22 is prevented from moving in accordance with the robotic control functionality described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. The manipulator controller 54 may also continuously track movement of the virtual constraint boundary and continuously adjust a path and/or orientation of the surgical instrument 22 as the virtual constraint boundary moves, to avoid the virtual constraint boundary.

The virtual constraint boundary can also be tracked simultaneously with tracking of a virtual cutting boundary associated with the femur F or tibia T described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. The virtual constraint boundary may move relative to the virtual cutting boundary during the surgery. Tracking of the boundaries would also enable tracking of the relative movement between such boundaries.

Models of the objects being tracked may be displayed on displays 28, 29 to show the location of the objects. Representations of the virtual boundaries and the anatomy being treated may also be shown on displays 28, 29. Additionally, information relating to the virtual constraint boundaries and virtual cutting boundary can be forwarded to the manipulator controller 54 to guide the manipulator 56 and corresponding movement of the surgical instrument 22 relative to these virtual boundaries so that the surgical instrument 22 does not intrude on the virtual boundaries.

In some embodiments, a virtual boundary is associated with the surgical instrument 22. The surgical instrument virtual boundary is tracked via the instrument tracker 48. The surgical instrument virtual boundary may be defined merely by a model of the surgical instrument 22. The manipulator controller 54 then monitors movement of the surgical instrument virtual boundary relative to the other virtual constraint boundaries, including the virtual cutting boundaries and other virtual constraint boundaries associated with other objects. The manipulator controller 54 is then programmed to continuously track movement of the boundaries and update guidance of the surgical instrument 22 as the boundaries move relative to the surgical instrument 22.

Objects to be avoided by the surgical instrument 22 in the operating room may be tracked indirectly by associating the object with one or more trackers that are not directly fixed to the object. For instance, in FIG. 4, the opening 106 in the tissue, although not directly attached to a tracker, is formed by the retractor assemblies 104 with trackers 110 fixed thereto. Since the retractor assemblies 104 form the opening 106, there is a general correlation between the size and shape of the opening 106 and the position and orientation of the retractor assemblies 104, which can be tracked by the navigation system 20 using the trackers 110, as described above. Therefore, the opening 106 can also be dynamically tracked.

The opening 106 can be defined in the boundary creation software module using the points associated with the retractor assemblies 104 since the opening 106 lies along an edge of the retractor assemblies 104. Alternatively, the opening 106 can be traced using the pointer P. In the latter case, the pointer P is used to capture points defining a periphery of the opening 106 such that the points can be connected in the boundary creation software module to form a ring representing the opening 106. The ring may be defined in the boundary creation software module as a virtual constraint boundary to constrain movement of the surgical instrument 22 to within the ring in accordance with the robotic control functionality associated with such openings described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. The opening 106 could additionally be registered to the trackers 110 so that movement of the opening 106 is trackable using the trackers 110. Other tissues to be avoided by the surgical instrument 22 such as nerve tissue, ligaments, and the like can similarly be outlined by the pointer P and associated with the trackers 110 to track their movement.

Figure 5:
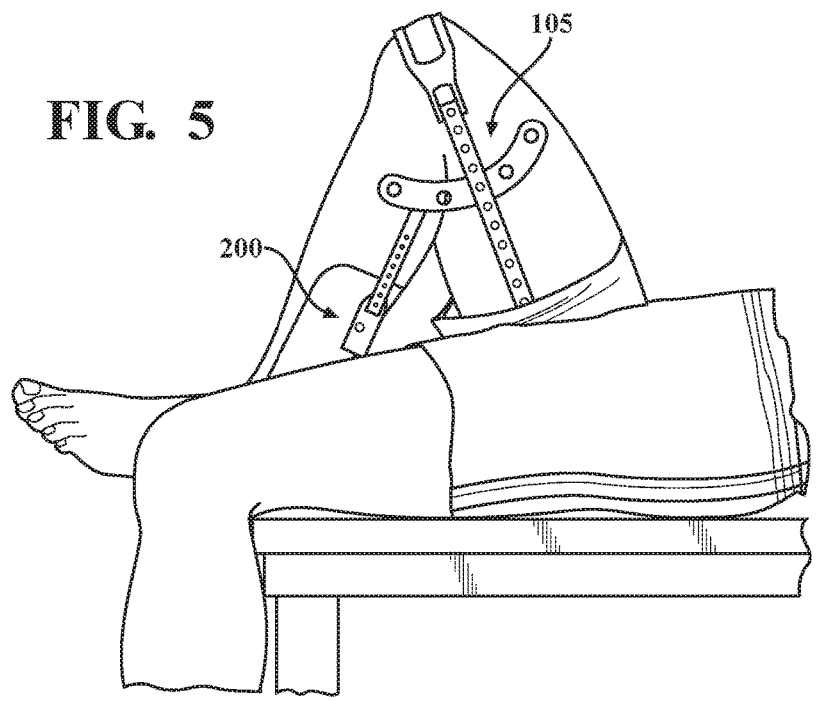
FIG. 5 is an elevational view of a leg holder and retractor assembly being used to maintain the tissue opening.

Referring to FIG. 5, a leg holder 200 for supporting a leg of a patient is shown. The leg holder 200 is described in more detail in U.S. patent application Ser. No. 13/554,010, entitled, "Multi-position Limb Holder", published as U.S. Patent Application Publication No. 2013/0019883, hereby incorporated by reference. An alternative retractor assembly 105 for attaching to the leg holder 200 is shown in FIG. 5. The alternative retractor assembly 105 is described in more detail in U.S. patent application Ser. No. 13/554,010, hereby incorporated by reference.

Figure 6:
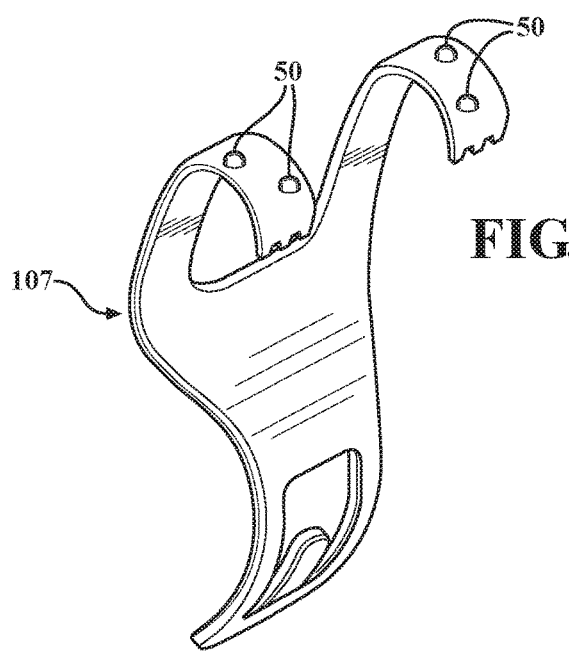
FIG. 6 is a top perspective view of a retractor.
Figure 7:
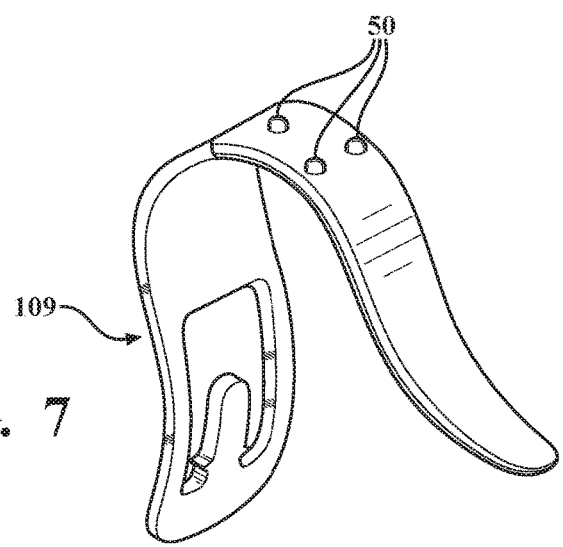
FIG. 7 is a top perspective view of an alternative retractor.

Retractor heads 107, 109 in FIGS. 6 and 7 can be used to retract soft tissue to access bone in a surgical procedure. Use of these types of heads 107, 109 for retracting tissue is described in more detail in U.S. patent application Ser. No. 13/554,010, hereby incorporated by reference. In FIGS. 6 and 7, tracking elements are fixed to the heads 107, 109 so that the heads 107, 109 can be tracked by the navigation system 20. In the embodiment shown, the tracking elements are three or more LEDs 50 that are integrated into the structure of each of the heads 107, 109 and fixed in relationship to one another. The geometric model of each head 107, 109 in relation to the LEDs 50 is also stored on the retractor head 107, 109 in memory (not shown) and can be transmitted to the camera unit 36 via transceivers (including transceiver, not shown, integrated into the retractor head 107, 109). Alternatively, the model of each head is pre-stored in the navigation computer 26 and accessed during navigation setup by identifying a type or serial no. of the retractor head 107, 109 using the boundary creation software module. The shape of each retractor head 107, 109 can also be identified by correlating a unique LED pattern on the retractor head 107, 109 to a database of retractor head shapes.

By creating virtual constraint boundaries associated with the shapes of the retractor assemblies 104 and tracking movement of the virtual constraint boundaries using trackers 110 or integrated tracking elements, the manipulator controller 54 can guide movement of the surgical instrument 22 with respect to the retractor virtual constraint boundaries and the virtual cutting boundaries so that the surgical instrument 22 is not moved beyond these boundaries thereby avoiding inadvertent contact with the retractor assemblies 104 or with bone or other tissue to remain after the surgery. These virtual boundaries may be used in both a manual mode and semi-autonomous mode of the surgical manipulator as described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference.

Figure 8:
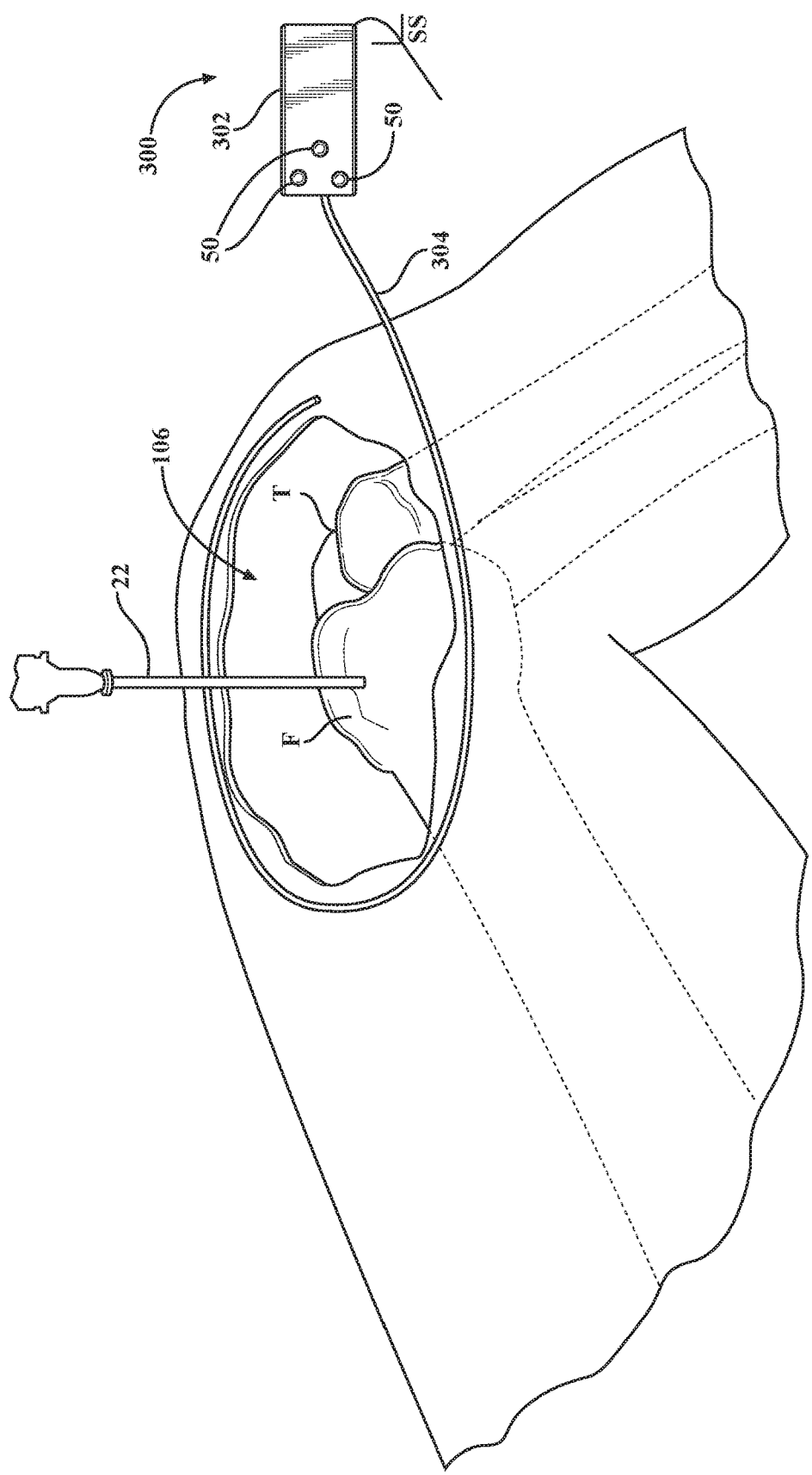
FIG. 8 is a top perspective view of the tissue opening showing an end effector in the tissue opening and a flexible shape sensing device for tracking movement of the tissue opening.

Referring to FIG. 8, a flexible shape sensing device 300 may also be used to determine a position of an object, such as opening 106. The flexible shape sensing device 300 includes a housing 302 having its own shape sensing coordinate system SS. The housing 302 forms part of a reflectometer, such as a Luna Distributed Sensing System commercially available from Luna Innovations Incorporated of Roanoke, Va. Another example of a commercially available reflectometer is the Optical Backscatter Reflectometer from Luna Innovations Incorporated.

A fiber optic cable 304 extends from the housing 302 and is laid on the patient's skin about the opening 106 in close proximity to the opening 106. In some embodiments, the cable 304 is adhered to the skin in a perimeter with an offset from the opening 106. In some embodiments, the offset is less than five millimeters from the opening 106 at all locations along the perimeter of the opening 106. In other embodiments, different offsets may be used or the offsets may be measured after placing the fiber optic cable 304 so that the location of the fiber optic cable 304 relative to the opening 106 is known. The cable 304 is flexible so that as the shape of the opening 106 changes, the shape of the cable 304 also changes. Position of the cable 304 is able to be dynamically tracked. The flexible shape sensing device 300 including the reflectometer, cable, and other features, and their method of use for determining position are described in U.S. Pat. No. 7,772,541 to Froggatt et al., hereby incorporated by reference.

Tracking elements, such as LEDs 50 may be integrated into the flexible shape sensing device 300. Alternatively, a tracker (not shown) can be mounted to the housing 302. The LEDs 50 integrated into the flexible shape sensing device 300 transmit signals to the camera unit 36 in the same manner as the LEDs 50 of the trackers 44, 46, 48. Accordingly, the position and orientation of the housing 302 and the shape sensing coordinate system SS can be determining by the navigation system 20 in the localizer coordinate system LCLZ. Movement of the cable 304 results in changes in position in shape sensing coordinate system SS, which is fixed with respect to housing 302. Coordinate system SS is registered to the localizer coordinate system LCLZ using the LEDs 50 on the housing 302. Once registered, changes in position of the cable 304 can also be determined in the localizer coordinate system LCLZ.

The opening 106 may be defined in the boundary creation software module as a virtual constraint boundary to constrain movement of the surgical instrument 22 to within the opening 106 in accordance with the robotic control functionality associated with such openings described in U.S. Provisional Patent Application No. 61/679,258, entitled, "Surgical Manipulator Capable of Controlling a Surgical Instrument in either a Semi-Autonomous Mode or a Manual, Boundary Constrained Mode," the disclosure of which is hereby incorporated by reference. Other tissues to be avoided by the surgical instrument 22 such as nerve tissue, ligaments, and the like can similarly be tracked using flexible shape sensing devices 300. Likewise, flexible shape sensing devices 300 could be used to establish other boundaries, such as being integrated into gloves worn by the surgical staff so that boundaries associated with surgical personnel can be created.

Figure 9:
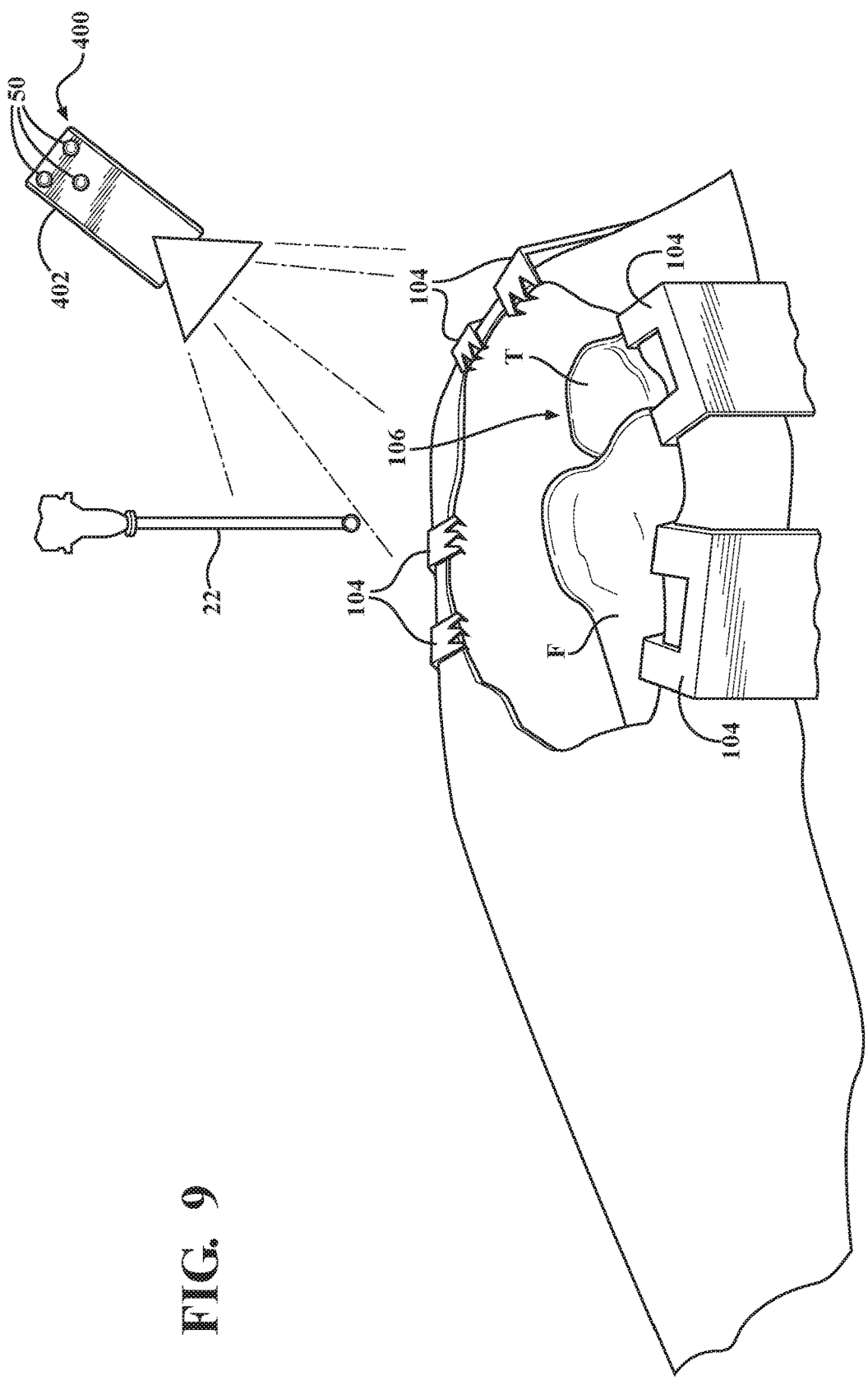
FIG. 9 is a top perspective view of the tissue opening showing an end effector in the tissue opening and a machine vision system for tracking movement of the tissue opening.

Machine vision can identify objects in the operating room and create virtual constraint boundaries associated with the objects. FIG. 9 shows a machine vision system 400. Machine vision system 400 includes a 3-dimensional machine vision camera 402. The vision camera 402 is arranged so that a field-of-view of the vision camera 402 encompasses the surgical site and objects in proximity to the surgical site. As shown in FIG. 9, such objects may include the surgical instrument 22 (shown as a cutting bur), retractor assemblies 104, femur F, and tibia T. The machine vision system 400 has a control unit (not shown) in communication with the vision camera 402. The control unit includes a processor, memory, and storage and is in communication with the navigation computer 26.

Initially, the objects to be tracked are identified. The objects may be identified by selecting objects stored in memory on the control unit using machine vision software. For instance, groups of pixels associated with different sizes and shapes of retractor assemblies 104 may be stored in the control unit. By selecting one of the retractor assemblies 104 to be tracked the machine vision software identifies the corresponding group of pixels and the machine vision software then operates to detect like groups of pixels using conventional pattern recognition technology.

Alternatively, the objects can be identified using an interface in which a user outlines or selects the objects to be tracked on the displays 28, 29. For instance, images taken by the vision camera 402 from overhead the surgical site—similar to the image shown in FIG. 9—are displayed on the displays 28, 29. The user then, using a mouse, digital pen, or the like, traces objects to be tracked on the display 28, 29. The machine vision software stores the pixels associated with the object that was traced into its memory. The user identifies each object by a unique identifier such as naming the object "MEDIAL RETRACTOR", etc. in the machine vision software so that the saved group of pixels is now associated with the unique identifier. Multiple objects could be stored in this manner. The machine vision system 400 utilizes conventional pattern recognition and associated software to later detect these objects.

The machine vision system 400 is able to detect movement of these objects by continuously taking images, reviewing the images, and detecting movement of the groups of pixels associated with the objects. In some cases, position information from the control unit of the machine vision system 400 for the objects can be transmitted to the navigation computer 26. Likewise, position information from the navigation computer 26 can be transmitted from the navigation computer 26 to the control unit of the machine vision system 400.

Control unit of the machine vision system 400 may provide position information for the objects in a machine vision coordinate system MV. The vision camera 402 also includes LEDs 50 so that the camera unit 36 can track and thus register the position and orientation of the machine vision coordinate system MV relative to the localizer coordinate system LCLZ. Thus, position information from the vision camera 402 can be determined in the localizer coordinate system LCLZ. Virtual boundaries can thus be associated with the objects in the machine vision system 400 and information relating to these virtual boundaries can be communicated to the navigation computer 26. Additionally, information relating to the virtual constraint boundaries can be forwarded to the manipulator controller 54 to guide the manipulator 56 and corresponding movement of the surgical instrument 22 relative to these virtual boundaries.

The objects can also be initially registered to the localizer coordinate system LCLZ using the pointer P. For instance, when the retractor assemblies 104 are not equipped with trackers 110 or integrated tracking elements, the pointer P may be used to initially establish virtual constraint boundaries associated with the retractor assemblies 104 when the retractor assemblies 104 are at rest, i.e., not moving. These virtual constraint boundaries would then be stored in the navigation computer 26 and/or manipulator controller 54 for use in guiding the robotic manipulator 56. The machine vision system 400 would also be configured to detect movement of the retractor assemblies 104 as previously described, i.e., by tracking movement of the groups of pixels associated with the retractor assemblies 104.

Machine vision detection of movement of a retractor assembly 104 could then be used to shift the virtual constraint boundary stored in the navigation computer for the retractor assembly 104 by defining a change in pose of the retractor assembly 104 (e.g., translation along 3 axes/rotation about 3 axes). The machine vision system 400 would operate to establish a first pose of the retractor assembly 140 at time t1 and a second pose at time t2. The difference in pose between t1 and t2 would be provided to the navigation computer 26 and/or manipulator controller 54 to move the associated virtual constraint boundary by a proportional amount in the localizer coordinate system LCLZ. In some embodiments, only 2-dimensional movement is detected by the vision camera 402 and shared with the navigation computer 26 and/or manipulator controller 54 to update a position of the retractor assembly 104.

In some embodiments, the robotic system is a robotic surgical cutting system for cutting away material from a patient's anatomy, such as bone or soft tissue. Once the cutting system is determined to be in the proper position by the navigation system 20, the cutting system cuts away material to be replaced by surgical implants such as hip and knee implants, including unicompartmental, bicompartmental, or total knee implants. Some of these types of implants are shown in U.S. patent application Ser. No. 13/530,927, entitled, "Prosthetic Implant and Method of Implantation", the disclosure of which is hereby incorporated by reference. The navigation system 20 instructs the surgeon on proper procedures for locating these implants on bone and securing the implants in position, including the use of trial implants.

In other systems, the instrument 22 has a cutting tool that is movable in three degrees of freedom relative to a handheld housing and is manually positioned by the hand of the surgeon, without the aid of cutting jigs, guide arms or other constraining mechanism. Such systems are shown in U.S. patent application Ser. No. 13/600,888, entitled, "Surgical Instrument Including Housing, a Cutting Accessory that Extends from the Housing and Actuators that Establish the Position of the Cutting Accessory Relative to the Housing", the disclosure of which is hereby incorporated by reference.

In these embodiments, the system includes a hand held surgical cutting instrument having a cutting tool. A control system controls movement of the cutting tool in at least three degrees of freedom using internal actuators/motors, as shown in U.S. patent application Ser. No. 13/600,888, entitled, "Surgical Instrument Including Housing, a Cutting Accessory that Extends from the Housing and Actuators that Establish the Position of the Cutting Accessory Relative to the Housing", the disclosure of which is hereby incorporated by reference. The navigation system 20 communicates with the control system. One tracker (such as tracker 48) is mounted to the instrument. Other trackers (such as trackers 44, 46) are mounted to a patient's anatomy. The navigation system 20 communicates with the control system of the hand held surgical cutting instrument. The navigation system 20 communicates position and/or orientation data to the control system. The position and/or orientation data is indicative of a position and/or orientation of the instrument 22 relative to the anatomy. This communication provides closed loop control to control cutting of the anatomy such that the cutting occurs within a predefined boundary (the term predefined boundary is understood to include predefined trajectory, volume, line, other shapes or geometric forms, and the like).

In some embodiments, a 3-D video camera (not shown) is attached to the camera unit 36. The video camera is oriented such that a field of view of the camera unit 36 can be associated with the field of view of the video camera. In other words, the two fields of view may be matched or otherwise correlated such that if an object can be seen in video images streamed from the video camera, the objects are also within the field of view of the camera unit 36. A coordinate system of the video camera can also be transformed into the localizer coordinate system LCLZ or vice versa so that positions and/or orientations of objects shown in the video images streamed from the video camera are known in the localizer coordinate system LCLZ. Video images from the video camera can be streamed to the displays 28, 29 and the user can then identify on the displays 28, 29, using an input device, such as a mouse or touch screen, virtual constraint boundaries to delineate zones to be avoided by the instrument 22. The video images could be provided in 2-D or in 3-D to facilitate the creation of these virtual constraint boundaries. Information relating to the positions and/or orientation of these virtual constraint boundaries would be provided into the localizer coordinate system LCLZ and tracked by the navigation computer 26 or manipulator controller 54, for example, to prevent the instrument 22 from intruding on the boundaries created.

In some embodiments, when the manipulator controller 54 or navigation computer 26 detect that the instrument 22 is approaching one of the virtual constraint boundaries, an alarm may be generated. The alarm may include visual, tactile, or audible feedback to the user that indicates to the user that the object associated with the virtual constraint boundary is about to be struck and/or may include visual, tactile, or audible indications of distance from the object or associated virtual constraint boundaries.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

The invention claimed is:
1. A surgical system comprising:
an instrument;

an instrument tracking device configured to track movement of said instrument;

a first boundary tracking device configured to track movement of a first of a plurality of virtual boundaries wherein the first virtual boundary is associated with an anatomy of a patient to be treated by said instrument;

a second boundary tracking device configured to track movement of a second of the plurality of virtual boundaries wherein the second virtual boundary is associated with a periphery of an opening in the patient to be avoided by said instrument; and a controller configured to receive information associated with said tracking devices including positions of said instrument relative to the first and second virtual boundaries, said controller configured to guide movement of said instrument relative to each of the first and second virtual boundaries as the first and second virtual boundaries move relative to one another.

2. A surgical system as set forth in claim 1 wherein said controller is further configured to guide movement of said instrument relative to the first virtual boundary by guiding cutting of the anatomy relative to the first virtual boundary.

3. A surgical system as set forth in claim 1 wherein said controller is further configured to guide movement of said instrument relative to the second virtual boundary so that said instrument avoids contact with the periphery of the opening associated with the second virtual boundary.

4. A surgical system as set forth in claim 1 further including a third boundary tracking device configured to track a third of the plurality of virtual boundaries associated with another object to be avoided by said instrument.

5. A surgical system as set forth in claim 4 wherein said controller is further configured to guide movement of said instrument relative to each of the first, second, and third virtual boundaries.

6. A surgical system as set forth in claim 4 wherein said controller is further configured to define the opening in the patient for receipt of said instrument based on positions of the second and third virtual boundaries.

7. A surgical system as set forth in claim 4 wherein said controller is further configured to monitor a position of the periphery of the opening based on positions of the second and third virtual boundaries.

8. A surgical system as set forth in claim 1 wherein at least one of said tracking devices includes one or more tracking elements.

9. A surgical system as set forth in claim 8 wherein said one or more tracking elements include light emitting diodes.

10. A surgical system as set forth in claim 8 wherein said one or more tracking elements include optical tracking elements and further including a plurality of sensing devices configured to receive optical signals from said optical tracking elements.

11. A surgical system as set forth in claim 1 further including a retractor configured to retract tissue and with said second boundary tracking device being coupled to said retractor.

12. A surgical system as set forth in claim 11 wherein said second boundary tracking device includes a tracker mountable to said retractor.

13. A surgical system as set forth in claim 11 wherein said second boundary tracking device includes at least one tracking element integrated into said retractor.

14. A surgical system as set forth in claim 1 wherein said second boundary tracking device includes a flexible shape sensing system positionable adjacent the periphery of the opening.

15. A surgical system as set forth in claim 1 wherein said second boundary tracking device includes a machine vision system and with said machine vision system in communication with said controller and including a vision camera configured to detect movement of the periphery of the opening.

16. A surgical system as set forth in claim 15 wherein said controller is configured to receive position information derived from images taken by said vision camera to adjust a position of the second virtual boundary after the second virtual boundary moves.

17. A surgical system as set forth in claim 1 wherein said second boundary tracking device includes a pointer configured to capture points associated with the periphery of the opening.

18. A surgical system as set forth in claim 17 wherein said controller is configured to create the second virtual boundary utilizing information relating to the points.

19. A surgical system as set forth in claim 1 including a surgical manipulator having a plurality of joints and a plurality of actuators and with said instrument being coupled to said surgical manipulator and wherein said surgical manipulator is configured to move said instrument.

20. A surgical system as set forth in claim 19 wherein said surgical manipulator is a robotic manipulator configured to be operated in manual and semi-autonomous modes.

21. A surgical system as set forth in claim 1 wherein said instrument is a hand-held surgical instrument configured to be supported and manually positioned by a user.

22. A surgical system as set forth in claim 21 wherein said hand-held surgical instrument includes a handheld housing and a cutting tool that is movable in three degrees of freedom relative to said handheld housing.

\* \* \* \* \*